(12) United States Patent
Yamazaki et al.

(10) Patent No.: US 11,639,503 B2
(45) Date of Patent: May 2, 2023

(54) ANTI-CHYMASE APTAMER AND USE FOR SAME

(71) Applicant: RIBOMIC INC., Tokyo (JP)

(72) Inventors: Satoko Yamazaki, Tokyo (JP); Yosuke Nonaka, Tokyo (JP); Yoshikazu Nakamura, Tokyo (JP); Masahiro Muraguchi, Osaka (JP); Kaori Murata, Osaka (JP)

(73) Assignee: RIBOMIC INC., Tokyo (JP)

( * ) Notice: Subject to any disclaimer, the term of this patent is extended or adjusted under 35 U.S.C. 154(b) by 0 days.

(21) Appl. No.: 16/767,683

(22) PCT Filed: Nov. 30, 2018

(86) PCT No.: PCT/JP2018/044132
§ 371 (c)(1),
(2) Date: May 28, 2020

(87) PCT Pub. No.: WO2019/107532
PCT Pub. Date: Jun. 6, 2019

(65) Prior Publication Data
US 2021/0002644 A1    Jan. 7, 2021

(30) Foreign Application Priority Data

Nov. 30, 2017   (JP) .............................. JP2017-230503

(51) Int. Cl.
*C12N 15/115*   (2010.01)
*A61K 31/7088*  (2006.01)

(52) U.S. Cl.
CPC ........ *C12N 15/115* (2013.01); *A61K 31/7088* (2013.01); *C12N 2310/16* (2013.01)

(58) Field of Classification Search
CPC .............. C12N 15/115; C12N 2310/16; A61K 31/7088
See application file for complete search history.

(56) References Cited

U.S. PATENT DOCUMENTS

| 6,500,835 B2 | 12/2002 | Fukami et al. |
| 2012/0165401 A1 | 6/2012 | Nakamura et al. |

FOREIGN PATENT DOCUMENTS

| WO | WO 1991/019813 A1 | 12/1991 | |
| WO | WO 1994/008050 A1 | 4/1994 | |
| WO | WO 1995/007364 A1 | 3/1995 | |
| WO | WO-2004048511 A2 * | 6/2004 | ............. A61P 31/00 |
| WO | WO 2010/143714 A1 | 12/2010 | |

OTHER PUBLICATIONS

Arnold et al., "One round of SELEX for the generation of DNA aptamers directed against KLK6," *Bio. Chem.*, 393(5): 343-353 (2012).
Ni et al., "Chemical Modifications of Nucleic Acid Aptamers for Therapeutic Purposes," *Int. J. Mol. Sci.*, 18(8): 1683 (2017).
Steen Burrell et al., "A kallikrein-targeting RNA aptamer inhibits the intrinsic pathway of coagulation and reduces bradykinin release," *J. Thromb. Haemost.*, 15(9): 1807-1817 (2017).
Xiao et al., "Immobilization of Chymotrypsin on Silica Beads Based on High Affinity and Specificity Aptamer and Its Applications," *Anal. Lett.*, 45(10): 1264-1273 (2012).
European Patent Office, Supplementary European Search Report in European Patent Application No. 18882587 (dated Oct. 15, 2021).
Jin et al., "A Chymase Inhibitory RNA Aptamer Improves Cardiac Function and Survival after Myocardial Infarction," *Mol. Ther. Nucleic Acids*, 14: 41-51 (2018).
Jin et al., "Inhibition of chymase by novel RNA aptamer and improvement of cardiac function and survival rate after myocardial infarction," *Programs and Abstracts of the 23rd Annual Meeting of the Japanese Society for Proteases in Pathophysiology*, p. 40, Abstract 25 (Jul. 30, 2018).
Japanese Patent Office, International Search Report in International Patent Application No. PCT/JP2018/044132 (dated Feb. 26, 2019).

* cited by examiner

*Primary Examiner* — J. E. Angell
(74) *Attorney, Agent, or Firm* — Leydig, Voit & Mayer, Ltd.

(57) ABSTRACT

The present invention provides an aptamer that binds to chymase, and contains a common sequence represented by UAACR$_1$N$_1$R$_2$GGGG wherein R$_1$ and R$_2$ are each any one base, and N$_1$ shows 3 to 30 bases (uracil is optionally thymine).

8 Claims, 7 Drawing Sheets
Specification includes a Sequence Listing.

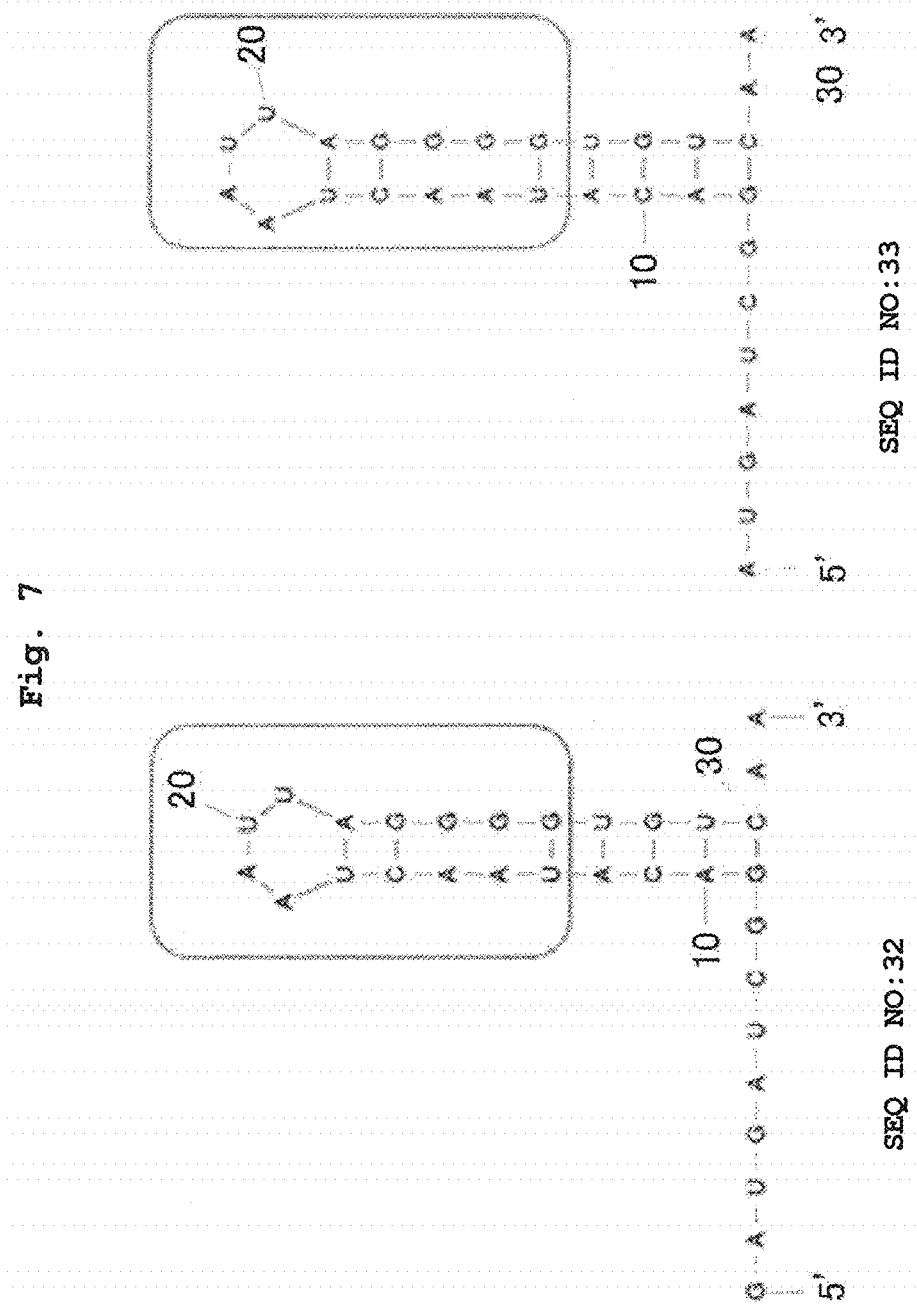

ANTI-CHYMASE APTAMER AND USE FOR SAME

CROSS-REFERENCE TO RELATED APPLICATIONS

This patent application is the U.S. national phase of International Patent Application No. PCT/JP2018/044132, filed on Nov. 30, 2018, which claims the benefit of Japanese Patent Application No. 2017-230503 filed on Nov. 30, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 10,683 bytes ASCII (Text) file named "749557Sequence-Listing.txt," created May 27, 2020.

TECHNICAL FIELD

The present invention relates to an aptamer against chymase, a method of utilizing the same and the like.

BACKGROUND ART

Human chymase (EC.3.4.21.39), a chymotrypsin-like serine protease, is stored in mast cell secretory granules. Upon external stimulation, mast cells undergo degranulation, resulting in the release of human chymase, along with a wide variety of inflammation mediators, outside the cells. The released human chymase specifically recognizes aromatic amino acids contained in substrate proteins and peptides, such as phenylalanine and tyrosine, and cleaves the peptide bonds adjoining to the amino acids. A representative substrate for human chymase is angiotensin I (AngI). Human chymase cleaves AngI to produce angiotensin II (AngII), a vasoconstricting factor.

Mammalian chymases are phylogenetically classified under two subfamilies: α and β. Primates, including humans, express only one kind of chymase, which belongs to the α family. Meanwhile, rodents express both the α and β families of chymase. In mice, there are a plurality of kinds of chymases, of which mouse mast cell protease-4 (mMCP-4), which belongs to the β family, is considered to be most closely related to human chymase, judging from its substrate specificity and mode of expression in tissue. In hamsters, hamster chymase-1, also a member of the β family, corresponds to human chymase. Meanwhile, mMCP-5 and hamster chymase-2, which belong to the α family as with human chymase, possess elastase-like activity and differ from human chymase in terms of substrate specificity.

Chymase is profoundly associated with the activation of transforming growth factor β (TGF-β). TGF-β exists in a latent form (latent-TGF-β) in extracellular matrices around epithelial cells and endothelial cells, and is retained in extracellular matrices via large latent TGF-β binding protein (LTBP). TGF-β is released from extracellular matrices as required and activated, and the activated TGF-β is a cytokine of paramount importance to living organisms reportedly involved in cell proliferation and differentiation and tissue repair and regeneration after tissue injury. Collapse of its signal leads to the onset and progression of a wide variety of diseases. It is thought that in this process, chymase is involved in the release of latent TGF-β from extracellular matrices and the conversion of latent TGF-β to active TGF-β.

Chymase is known to be associated with a broad range of diseases, including fibrosis, cardiovascular diseases, inflammation, allergic diseases and organ adhesion. Fibrosis is an illness characterized by abnormal metabolism of extracellular substrates in the lung, heart, liver, kidney, skin and the like, resulting in excess deposition of connective tissue proteins. In pulmonary fibrosis, for example, connective tissue proteins such as collagen deposit in excess in the lung, resulting in hard shrinkage of pulmonary alveoli and ensuing respiratory distress. Lung fibrosis has been shown to result from pneumoconiosis, which is caused by exposure to a large amount of dust, drug-induced pneumonia, which is caused by use of drugs such as anticancer agents, allergic pneumonia, pulmonary tuberculosis, autoimmune diseases such as collagen disease, and the like. However, there are not a few cases in which the cause is unknown.

The mechanism of onset of fibrosis at the molecular level has not been elucidated well. Generally, in normal states, the proliferation and functions of fibroblasts are well controlled. In case of serious or persistent inflammation or injury, however, the tissue repair mechanism works in excess, resulting in abnormal proliferation of fibroblasts and overproduction of connective tissue proteins. TGF-β is known as a factor that causes these phenomena. As evidence suggestive of its involvement, it has been reported that administration of an anti-TGF-β neutralizing antibody to an animal model of fibrosis causes decreased collagen expression and significantly suppressed fibrosis. In patients with idiopathic pulmonary fibrosis, increased levels of TGF-β and elevated counts of chymase-positive mast cells are observed.

Meanwhile, association of chymase in fibrosis has been demonstrated by experiments using animal models. In a hamster model of bleomycin-induced pulmonary fibrosis, facilitated chymase activity, increased expression of collagen III mRNA, tissue fibrosis and other phenomena are significantly reduced by chymase inhibitors. The same effects have been observed for a mouse model of bleomycin-induced pulmonary fibrosis; administration of chymase inhibitors suppressed chymase activity and reduced hydroxyproline content.

With these features, chymase inhibitors can be used as prophylactic or therapeutic drugs for diseases related to chymase, such as fibrosis. Chymase inhibitors that have been developed include small molecular compounds such as TPC-806, SUN-13834, SUN-C8257, SUN-C8077, and JNJ-10311795 (Patent document 1).

In recent years, applications of RNA aptamers to therapeutic drugs, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (Patent documents 2-4). In the SELEX method, an RNA that binds specifically to a target molecule is selected from an RNA pool with about $10^{14}$ different nucleotide sequences. The RNA used has a random sequence of about 40 nucleotides, which is flanked by primer sequences. This RNA pool is mixed with a target molecule, and only the RNA that has bound to the target molecule is separated using a filter and the like. The RNA separated is amplified by RT-PCR, and this is used as a template for the next round. By repeating this operation about 10 times, an RNA aptamer that binds specifically to the target molecule can be acquired.

Aptamer drugs, like antibody drugs, can target extracellular proteins. With reference to many scientific papers and other reference materials in the public domain, aptamer drugs are judged to potentially surpass antibody drugs in some aspects. For example, aptamers often exhibit higher affinity and specificity for target molecules than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), are reportedly unlikely to occur with the use of aptamers. From the viewpoint of drug delivery, aptamers are likely to migrate to tissues because of their molecular size of about one-tenth that of antibodies, enabling easier drug delivery to target sites. Because aptamers are produced by chemical synthesis, they permit site-selective chemical modifications, and enable cost reduction by mass-production. Other advantages of aptamers include long-term storage stability, heat resistance and solvent resistance. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

As an aptamer that binds to chymase to inhibit a chymase activity, the present inventors produced an aptamer containing a nucleotide sequence represented by $X_1GAUAGAN_1N_2UAAX_2$ (each of $X_1$ and $X_2$, whether identical or not, is A or G, and each of $N_1$ and $N_2$, whether identical or not, is A, G, C, U or T) (patent document 5 (the sequence is shown by SEQ ID NO: 21 in patent document 5)).

DOCUMENT LIST

Patent Documents patent document 1: U.S. Pat. No. 6,500,835
patent document 2: WO 91/19813
patent document 3: WO 94/08050
patent document 4: WO 95/07364
patent document 5: WO 2010/143714

SUMMARY OF THE INVENTION

Problems to be Solved by the Invention

The present invention is directed to providing an aptamer for chymase and a method for utilizing the same, and the like.

Means of Solving the Problems

The present inventors have conducted intensive studies in an attempt to solve the aforementioned problems and succeeded in preparing an aptamer that has good quality for chymase, has a sequence completely different from that of the chymase aptamer described in patent document 5, and is characterized by markedly high activity, which resulted in the completion of the present invention.

Accordingly, the present invention provides the following:

[1] An aptamer that binds to chymase, and comprises a common sequence represented by $UAACR_1N_1R_2GGGG$ wherein $R_1$ and $R_2$ are each any one base, and $N_1$ shows 3 to 30 bases (uracil is optionally thymine).

[2] An aptamer that binds to chymase, and comprises a potential secondary structure represented by the formula (1) (uracil is optionally thymine):

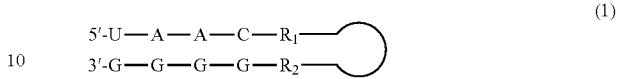

(1)

wherein

(1')

in the formula (1) is a stem-loop partial structure, and $R_1$ and $R_2$ are each any one base.

[3] The aptamer of [1] or [2] that inhibits the activity of chymase.

[4] The aptamer of any of [1] to [3], wherein a combination of $R_1$ and $R_2$ is A/U, C/G, A/C or G/U (uracil is optionally thymine).

[5] The aptamer of any of [1] to [4], wherein at least one of pyrimidine nucleotides is modified or altered.

[6] The aptamer of any of [1] to [5], wherein U and/or C in the sequence $UAACR_1$ are/is modified or altered.

[7] The aptamer of any of [2] to [6], wherein the stem-loop part of (1') has a base length of 3-21.

[8] The aptamer of any of [1] to [7], wherein a sequence of $N_1$ or the stem-loop partial structure represented by

(1')

is UUGU, CUGG or AAUU (uracil is optionally thymine).

[9] The aptamer of [1] or [2], comprising any of the nucleotide sequences of the following (a), (b) and (c):
(a) a nucleotide sequence selected from any of SEQ ID NOs: 1-11 and 14-33 (uracil is optionally thymine);
(b) a nucleotide sequence selected from any of SEQ ID NOs: 1-11 and 14-33 (uracil is optionally thymine) wherein one to several nucleotides are substituted, deleted, inserted or added; and
(c) a nucleotide sequence having identity of not less than 70% with a nucleotide sequence selected from any of SEQ ID NOs: 1-11 and 14-33 (uracil is optionally thymine).

[10] The aptamer of [9], wherein at least one nucleotide contained in the aptamer is modified or altered.

[11] The aptamer of [1] or [2], wherein a hydroxyl group at the 2'-position of ribose of each pyrimidine nucleotide contained in the aptamer is the same or different and unsubstituted or substituted by an atom or a group selected from the group consisting of a hydrogen atom, a fluorine atom and a methoxy group.

[12] The aptamer of [1] or [2], wherein the hydroxyl group at the 2'-position of ribose of each purine nucleotides contained in the aptamer is the same or different and unsubstituted or substituted by an atom or a group selected from the group consisting of a hydrogen atom, a fluorine atom and a methoxy group.

[13] A complex comprising the aptamer and the functional substance of any of [1] to [12].
[14] A medicament comprising the aptamer of any of [1] to [12] or the complex of [13].
[15] The medicament of [14] that is a therapeutic drug for a disease involving organ or tissue fibrosis, or a circulatory disease.
[16] The medicament of [14] that is a therapeutic drug for fibrosis.
[17] A method for detecting chymase, comprising using the aptamer of any of [1] to [12] or the complex of [13].
[18] A method for treating a disease involving organ or tissue fibrosis, or a circulatory disease, comprising administering the aptamer of any of [1] to [12], the complex of [13], or the medicament of [14] to a target.
[19] The aptamer of any of [1] to [12], the complex of [13], or the medicament of [14] for use in the treatment of a disease involving organ or tissue fibrosis, or a circulatory disease.
[20] Use of the aptamer of any of [1] to [12] or the complex of [13] for the production of a medicament for a disease involving organ or tissue fibrosis, or a circulatory disease.

Effect of the Invention

The aptamer or the complex of the present invention can be useful as a pharmaceutical or a diagnostic reagent or a reagent for various diseases caused by chymase, such as fibrosis and cardiovascular diseases. The aptamer or the complex of the present invention can also be useful in purifying and concentrating chymase, and detecting and quantifying chymase.

BRIEF DESCRIPTION OF THE DRAWINGS

FIG. 7 shows the predicted secondary structures of the aptamers of the sequences shown by SEQ ID NO: 32-33.

DESCRIPTION OF EMBODIMENTS

Figure 1:
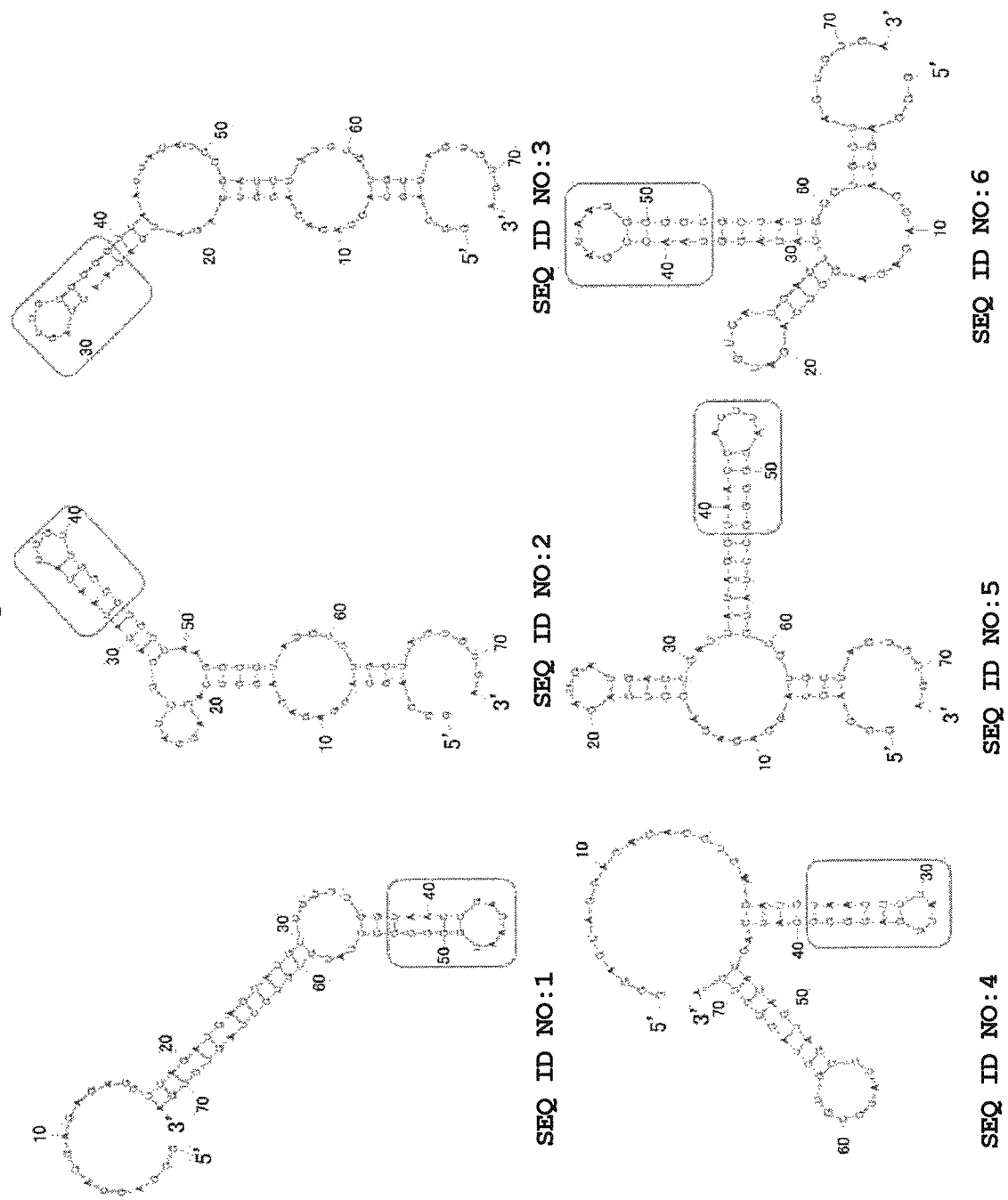
FIG. 1 shows the predicted secondary structures of the aptamers of the sequences shown by SEQ ID NO: 1-6.

The present invention provides an aptamer possessing a binding activity for chymase. The aptamers of the present invention are capable of inhibiting activities of chymase.

An aptamer refers to a nucleic acid molecule having a binding affinity for a particular target molecule. The aptamer can also inhibit the activity of a particular target molecule by binding to the particular target molecule. The aptamer of the present invention possesses binding activity for chymase, and is capable of inhibiting a chymase activity. The aptamer of the present invention can be an RNA, a DNA, a modified nucleic acid or a mixture thereof. The aptamer of the present invention can also be in a linear or circular form.

Chymase, a publicly known serine protease, is stored in mast cell secretory granules. Chymase is profoundly involved in a wide variety of biological reactions mediated by mast cells, including, for example, bioactive peptide production and degradation, extracellular matrix remodeling, networks with cytokines, and immunity. The aptamer of the present invention can exhibit inhibitory activity against chymase derived from any mammals. Such mammals include primates (e.g., humans, monkeys), rodents (e.g., mice, rats, guinea pigs, hamsters), and companion animals, domesticated animals and work animals (e.g., dogs, cats, horses, bovines, goat, sheep, pigs), with preference given to humans. The amino acid sequence of human chymase is shown by Accession Number AAB26828, and may be a sequence having one to several mutated residues, a domain moiety thereof, or a peptide moiety thereof. The structure of human chymase may be not only a monomer, but also a dimer or polymer.

The aptamer of the present invention binds to chymase in physiological buffer solutions. Although there is no limitation on the choice of buffer solution, preference is given to buffer solutions having a pH of about 5.0-10.0. Such buffer solutions include, for example, the solution A and solution C described below (see Examples 1 and 2). The aptamer of the present invention binds to chymase at strength detectable by any one of the tests described below.

Binding strength is measured using Biacore T100 (manufactured by GE Healthcare). In a method of measurement, the aptamer is first immobilized onto a sensor chip, the amount immobilized being about 1000 RU. 20 μL of a chymase solution for analyte, prepared at 0.2 μM, is injected, and the binding of chymase to the aptamer is detected. An RNA comprising a random nucleotide sequence of 30 or 40 nucleotides is used as a negative control. If the chymase binds to the aptamer equivalently or significantly more potently compared with the control RNA, the aptamer is judged to have the capability of binding to chymase.

In another method, chymase is first immobilized onto a sensor chip, the amount immobilized being about 4000 RU. 20 μL of an aptamer solution for analyte, prepared at 0.01 μg/μL, is injected, and the binding of the aptamer to chymase is detected. An RNA containing a random nucleotide sequence of 30 or 40 nucleotides is used as a negative control. If the chymase binds to the aptamer equivalently or significantly more potently compared with the control RNA, the aptamer is judged to have the capability of binding to chymase.

An inhibitory activity against chymase means an inhibitory potential against any activities possessed by chymase. For example, enzyme activity to hydrolyze and cleave peptide chains, which is one of the functions of chymase, is inhibited. Acceptable substrates for enzyme activity are not limited to proteins and bioactive peptides present in living organisms (e.g., AngI, latent TGF-β and the like), but include peptides, containing partial amino acid sequences of the foregoing peptides, conjugated with chromogenic substance or fluorescent substance. Chromogenic substances and fluorescent substances are known to those skilled in the art. Phenomena that occur via protein or bioactive peptide degradation reactions include increased expression of collagen I/III, increased hydroxyproline content, increased expression of IgE and the like; suppressive effects thereon are also included in the inhibitory activities against chymase. In addition, inhibitory activities against the migration of neutrophils, monocytes, and eosinophils to chymase is also included in inhibitory activity against chymase. Furthermore, suppressive effects against chymase-induced histamine release promotion, mast cell count elevation, increased vascular permeability, tissue fibrosis, inflammation, angiogenesis, vascular intimal thickening and the like are also included in the inhibitory activities against chymase.

A substrate for chymase means a peptide, protein or the like that undergoes hydrolytic cleavage by chymase. Substrates for chymase known to exist in living organisms include peptides and proteins such as AngI, latent TGF-β, stem cell factor (SCF), procollagen, procollagenase, fibronectin, promatrix metalloprotease-1 (pro-MMP-1), pro-MMP-9, tissue inhibitor of matrix metalloproteinase-1 (TIMP-1), apolipoprotein A-I (apoA-I), apoE, phospholipid transfer protein, IL-1β precursor, big-endothelin-1 (big-ET-1), big-ET-2, connective tissue-activating peptide III, IL-18 precursor, substance P, vasoactive intestinal peptide (VIP), kallidin, bradykinin, and C3a. Herein, chymase substrates are not limited to them, but include artificially designed model peptides comprising amino acid residues specifically recognized by chymase, such as Phe and Tyr, as well as these peptides conjugated with chromogenic substance or fluorescent substance.

Whether an aptamer inhibits the enzyme activity of chymase can be determined by, for example, the two testing methods described below.

A first method employs a synthetic substrate. A useful chymase substrate is Suc-Ala-Ala-Pro-Phe-MCA (4-methylcoumaryl-7-amide group) (manufactured by Peptide Institute, Inc.), which contains the 4-amino acid peptide "Ala-Ala-Pro-Phe" (SEQ ID NO: 41), a standard substrate for chymotrypsin-like proteases.

The assay is performed using a 96-well plate (F16 Black Maxisorp Fluoronunc, manufactured by Nunc), with a reaction mixture volume of 100 µL, in a buffer solution (solution C; see Example 2 below). First, each nucleic acid is prepared in solution C to obtain 50 µL solutions. After 10 µL of the 1 mM substrate prepared in solution C is added, the plate is set to the microplate reader SpectraMax190 (manufactured by Molecular Devices Corporation), and incubated at 37° C. for 5 minutes. Separately, 0.05 µg of chymase (recombinant, manufactured by SIGMA) is diluted in solution C, and 40 µL of this dilution is incubated at 37° C. for 5 minutes. The chymase solution is added to the mixture of the nucleic acid and substrate to initiate an enzyme reaction. The plate containing the reaction mixture is set to the microplate reader SpectraMax190 (manufactured by Molecular Devices Corporation), and examined for time-dependent changes in the fluorescence intensity at 37° C. for 5 minutes (excitation wavelength 380 nm, detection wavelength 460 nm). A linear approximation of the increase in the fluorescence of the AMC (7-amino-4-methylcoumarine) released from the substrate by chymase activity is generated, and its slope is taken as the initial reaction velocity. For control, samples are treated and analyzed in the same manner in two cases: use of a nucleic acid pool containing a random sequence of 30 or 40 nucleotides (negative control), and use of chymostatin, a known chymotrypsin-like serine protease inhibitor (positive control). Taking the initial reaction velocity without the nucleic acid and inhibitor as a 100% enzyme activity, the inhibitory rate for each test substance is calculated, and the inhibitor concentration required to cause a 50% inhibition of the enzyme activity ($IC_{50}$) is determined. An aptamer exhibiting a lower $IC_{50}$ value than that of chymostatin, a known inhibitor, is judged to possess excellent inhibitory activity.

A second method of evaluation employs a native substrate. A useful native substrate for chymase is angiotensin I. Here, His-Leu, a peptide fragment released upon degradation of angiotensin I, is fluorescently derivatized, and the fluorescence intensity therefrom is quantified.

In the assay, an enzyme reaction is carried out in 50 µL of solution C. First, 0.3-0.75 ng of chymase (recombinant, manufactured by SIGMA; or native, manufactured by Calbiochem) is diluted in solution C to obtain 5 µL chymase solution. Each nucleic acid is prepared in solution C to obtain 25 µL solutions. 5 µL of each chymase dilution and 25 µL of each nucleic acid solution are mixed, and then the mixture is incubated at 37° C. for 5 minutes. Separately, 20 µL of 125 µM angiotensin I (manufactured by Peptide Institute, Inc.) is prepared in solution C and incubated at 37° C. for 5 minutes. The angiotensin I solution is added to the mixture of chymase and nucleic acid, and the enzyme reaction is initiated. After the reaction was allowed to proceed at 37° C. for 90 minutes, 25 µL of ice-cooled 30% trichloroacetic acid solution is added to terminate the reaction. The entire mixture is centrifuged at 4° C., 14000 rpm for 10 minutes, and 30 µL of the resulting supernatant is used for the subsequent reaction for fluorescent derivatization.

After 30 µL of the supernatant is added to a 96-well plate (Black, manufactured by Costar), 15 µL of 2% o-phthalaldehyde (manufactured by SIGMA) solution in methanol and 170 µL of 0.3M NaOH solution are mixed in each well, and the plate is allowed to stand at room temperature for 10 minutes. Subsequently, 25 µL of 3M HCl solution is added to terminate the reaction. The plate is set to the microplate reader SpectraMax190 (manufactured by Molecular Devices Corporation), and the fluorescence intensity is determined at an excitation wavelength of 355 nm and a fluorescence wavelength of 460 nm.

For control, samples are treated and analyzed in the same manner in two cases: use of SEQ ID NO: 58 (negative control) and use of chymostatin, a known chymotrypsin-like serine protease inhibitor (positive control). In both cases, fluorescence intensity obtained at 0 minute reaction time serves as a blank determination. Taking the fluorescence intensity detected with the addition of an equal volume of solution C, in place of each nucleic acid, in the chymase enzyme reaction as 100%, the inhibitory rate for each test substance is calculated, and the inhibitor concentration required to cause a 50% inhibition of the enzyme activity ($IC_{50}$) is determined. An aptamer exhibiting a lower $IC_{50}$ value than that of chymostatin, a known inhibitor, is judged to possess excellent inhibitory activity.

As shown in detail in the below-mentioned Examples, the aptamer of the present invention has about 10 to 100 times higher inhibitory activity against chymase, as compared to the aptamer against chymase that has already been reported in WO 2010/143714. To be specific, while the aptamer against chymase disclosed in WO 2010/143714 is considered a superior aptamer since it shows an $IC_{50}$ value of not more than 0.1 µM (see paragraph [0105] and the like), many of the aptamers of the present invention showed an $IC_{50}$ value of not more than 1 nM as shown in Example 3 (Table 4).

Therefore, the inventors did not expect when the present invention was completed that such an aptamer that has good quality for chymase was obtained. From the above, it can be said that the aptamer of the present invention affords advantageous effects that cannot be easily envisaged from known documents even by those of ordinary skill in the art.

There is no limitation on the aptamer of the present invention, as far as it is capable of binding to any portions of chymase to inhibit the activity thereof.

The length of the aptamer of the present invention is not limited, and can usually be about 25 to about 200 nucleotides, and can be, for example, not more than about 100 nucleotides, preferably not more than about 50 nucleotides, more preferably not more than about 40 nucleotides, most preferably not more than about 35 nucleotides. When the total number of nucleotides is smaller, chemical synthesis and mass-production will be easier, and there is a major advantage in terms of cost. It is also thought that chemical modification is easy, stability in the body is high, and toxicity is low. On the other hand, the length of the aptamer of the present invention is generally not less than about 25 nucleotides, preferably about not less than 28 nucleotides. When the total number of nucleotides is too small, the common sequence explained below cannot be contained, and the potential secondary structure becomes unstable and the activity may be lost in some cases.

Each of the nucleotides contained in the aptamer of the present invention, whether identical or different, can be a nucleotide comprising a hydroxyl group at the 2' position of ribose (e.g., ribose of pyrimidine nucleotide, ribose of purine nucleotide) (i.e., an unsubstituted nucleotide) or a nucleotide substituted by any atom or group at the 2' position of ribose. As examples of such any atom or group, a nucleotide substituted by a hydrogen atom, a fluorine atom or an —O-alkyl group (e.g., —O-Me group), an —O-acyl group (e.g., —O—COMe group), or an amino group (e.g., —NH$_2$ group) can be mentioned.

The aptamer of the present invention contains the common sequence represented by UAACR$_1$N$_1$R$_2$GGGG (hereinafter sometimes to be referred to as the common sequence of the present invention). An aptamer having this sequence inhibits the activity of chymase by strongly binding to chymase. That is, an aptamer known to inhibit the activity of chymase is clearly an aptamer that binds to chymase even without confirmation of the binding to chymase.

In the above-mentioned common sequence, R$_1$ and R$_2$ are each any one base. The combination of R$_1$ and R$_2$ is not particularly limited as long as the aptamer of the present invention binds to chymase. For example, the combination of R$_1$ and R$_2$ is A/U, C/G, A/C or G/U (uracil may be thymine), more preferably a combination that forms Watson-Crick base pairs by R$_1$ and R$_2$ (A/U or C/G).

The above-mentioned combination of R$_1$ and R$_2$ is not particularly limited as long as the aptamer of the present invention binds to chymase, and R$_1$ and R$_2$ may be interchanged. That is, when the combination of R$_1$ and R$_2$ is indicated as A/U, R$_1$ is A and R$_2$ is U, or R$_1$ is U and R$_2$ is A. The same applies to C/G, A/C and G/U.

The sequence of the N$_1$ part of the common sequence UAACR$_1$N$_1$R$_2$GGGG is not particularly limited as long as the aptamer of the present invention binds to chymase and may be any sequence. The base length of the part is not particularly limited as long as the aptamer of the present invention binds to chymase and is typically 3-30, preferably 3-21, more preferably 3-19.

The aptamer of the present invention has a potential secondary structure represented by the following formula (1)

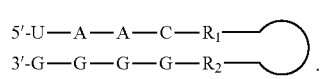
(1)

An aptamer having this sequence inhibits the activity of chymase by strongly binding to chymase.

In the above-mentioned formula (1), a stem structure is formed between UAACR$_1$ and R$_2$GGGG (containing two A/G mismatches). That is, a stem structure is formed between UAACR$_1$ and R$_2$GGGG in the common sequence. In other words, the N$_1$ part in the common sequence forms a loop structure.

In the above-mentioned formula (1), R$_1$ and R$_2$ are each any one base. The combination of R$_1$ and R$_2$ is not particularly limited as long as a stem structure is formed between UAACR$_1$ and R$_2$GGGG in the above-mentioned formula (1). The combination of R$_1$ and R$_2$ is preferably A/U, C/G, A/C or G/U (uracil may be thymine), more preferably a combination that forms Watson-Crick base pairs by R$_1$ and R$_2$ (A/U or C/G).

In the above-mentioned combination of R$_1$ and R$_2$, R$_1$ and R$_2$ may be interchanged as long as a stem structure is formed between UAACR$_1$ and R$_2$GGGG in the above-mentioned formula (1). That is, when the combination of R$_1$ and R$_2$ is indicated as A/U, R$_1$ is A and R$_2$ is U, or R$_1$ is U and R$_2$ is A. The same applies to C/G, A/C and G/U.

Here, in the formula (1),

(1')

indicates a stem-loop partial structure. The base length of the partial structure is not particularly limited as long as the aptamer of the present invention binds to chymase and is typically 3-30, preferably 3-21, more preferably 3-19. When the base length of the partial structure is less than 3, the loop structure cannot be formed and when it exceeds 30, the influence of the base in the partial structure becomes remarkable and the activity of the aptamer may decrease in some cases. Particularly, when the base length is not more than 21, stable aptamer activity is found. In the stem-loop partial structure, the stem structure may be present or absent and the whole may be a loop structure. That is, for the aptamer of the present invention to have binding activity to chymase, it is important that the structure of the following formula (1)

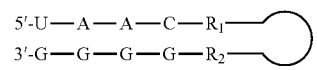
(1)

take a stem-loop structure as a whole. Since a stem structure is already formed between UAACR$_1$ and R$_2$GGGG, whether a stem structure is present or absent in the partial structure

(1')

in the formula (1) is not important. On the other hand, when a stem structure is present, the stem structure may have a bulge structure.

As mentioned above, in the aptamer of the present invention, it is highly important for the expression of the activity as an aptamer against chymase that the structure of the formula (1)

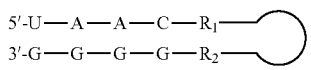 (1)

has a stem-loop structure as a whole. That is, in the present invention, the sequence of the stem-loop partial structure

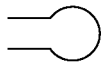 (1')

in the formula (1) is not particularly limited as long as the aptamer has the structure of the above-mentioned formula (1) and has binding activity to chymase (or chymase inhibitory activity). As actually shown in the below-mentioned Examples, the sequence of the above-mentioned stem-loop partial structure is not limited to a particular one, and various sequences may have a similar stem-loop partial structure and have binding activity to chymase.

A preferable sequence of the above-mentioned formula (1') is UUGU, UUGC, CUGG or AAUU (uracil may be thymine), more preferably UUGU.

Furthermore, the sequence of the both ends of the structure shown by the above-mentioned formula (1), namely, the 5'-terminal side and the 3'-terminal side, is not limited to a particular one, and various sequences may have similar binding activity to chymase (or chymase inhibitory activity).

The aptamer of the present invention can also be the nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a methoxy group, at the 2' position of ribose. Particularly, U and/or C in the common sequence and the structure represented by the formula (1) may be modified by a group selected from the group consisting of a hydrogen atom, a fluorine atom, and a methoxy group, preferably at the 2'-position of ribose.

In the aptamer of the present invention, all pyrimidine nucleotides can be nucleotides substituted by a fluorine atom, or nucleotides substituted by any atom or group mentioned above, preferably an atom or group selected from the atom or group consisting of a hydrogen atom, a hydroxyl group and a methoxy group whether identical or not, at the 2' position of ribose.

In the aptamers of the present invention, all purine nucleotides can be nucleotides comprising a hydroxyl group, or nucleotide substituted by any atom or group mentioned above, preferably an atom or a group selected from the group consisting of a hydrogen atom, a methoxy group, and a fluorine atom, whether identical or not, at the 2'-position of ribose.

The aptamer of the present invention can also be one wherein all nucleotides identically comprise a hydroxyl group, or any atom or group mentioned above, for example, the identical group selected by the group consisting of a hydrogen atom, a fluorine atom, a hydroxyl group and a methoxy group, at the 2' position of ribose.

Herein, in this specification, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, substitution of the hydroxyl group at the 2' position of ribose by X should read as a substitution of one hydrogen atom at the 2' position of deoxyribose by X.

The aptamer of the present invention can also be:
(a) an aptamer comprising a nucleotide sequence selected from among SEQ ID NO:1-11 and 14-33 (with the provision that the uracil may be thymine);
(b) an aptamer comprising a nucleotide sequence selected from among SEQ ID NO:1-11 and 14-33 (with the provision that the uracil may be thymine), wherein 1 or several nucleotides are substituted, deleted, inserted or added; or
(c) an aptamer comprising a nucleotide sequence having an identity of 70% or more (preferably 80% or more, more preferably 90% or more, most preferably 95% or more) to a nucleotide sequence selected from among SEQ ID NO: 1-11 and 14-33 (with the provision that the uracil may be thymine). The aptamer of the present invention also includes:
(d) a conjugate selected from the group consisting of a conjugate of a plurality of aptamers (a) above, a conjugate of a plurality of aptamers (b) above, a conjugate of a plurality of aptamers (c) above, and a conjugate of a plurality of aptamers (a), (b) and (c) above.

Not only the aptamer (a) above, but also the aptamers (b) to (d) are capable of binding to chymase and/or inhibiting a chymase activity (chymase enzyme activity and the like).

The aptamer of the present invention can also be:
(a') an aptamer comprising a nucleotide sequence selected from among SEQ ID NO: 17(1)-17(25) and 33(1)-33(18) (with the provision that the uracil may be thymine);
(b') an aptamer comprising a nucleotide sequence selected from among SEQ ID NO: 17(1)-17(25) and 33(1)-33(18) (with the provision that the uracil may be thymine), wherein 1 to 5 nucleotides are substituted, deleted, inserted or added; or
(c') an aptamer comprising a nucleotide sequence having an identity of 70% or more to a nucleotide sequence selected from among SEQ ID NO: 17(1)-17(25) and 33(1)-33(18) (with the provision that the uracil may be thymine). The aptamer of the present invention also includes:
(d') a conjugate selected from the group consisting of a conjugate of a plurality of aptamers (a') above, a conjugate of a plurality of aptamers (b') above, a conjugate of a plurality of aptamers (c') above, and a conjugate of a plurality of aptamers (a'), (b') and (c') above. Furthermore, the aptamer of the present invention also includes:
(e) a conjugate consisting of one or more aptamers selected from the group consisting of (a), (b) and (c) above, and one or more aptamers selected from the group consisting of (a'), (b') and (c').

The aptamers (a')-(d') and (e) above are also capable of binding to chymase and/or inhibiting a chymase activity (chymase enzyme activity and the like).

In (b) and (b') above, there is no limitation on the number of nucleotides substituted, deleted, inserted or added, as far as the aptamer is capable of binding to chymase and/or inhibiting a chymase activity (chymase enzyme activity and the like). The number of nucleotides can be, for example, not more than about 30, preferably not more than about 20, more preferably not more than about 10, still more preferably not more than 5, most preferably 4, 3, 2 or 1.

With respect to (c) and (c') above, "an identity" means a ratio (%) of identical nucleotide residues to all overlapping nucleotide residues in the optimal alignment where two nucleotide sequences are aligned using a mathematical algorithm known in the technical field (preferably, the algorithm considers introduction of gaps on one or both of the sequences for the best alignment).

Nucleotide sequence identity in the present description can be calculated by, for example, aligning the two nucleotide sequences using the homology calculation algorithm NCBI BLAST-2 (National Center for Biotechnology Information Basic Local Alignment Search Tool) under the following conditions (gap open=5 penalties; gap extension=2 penalties; x_dropoff=50; expectancy=10; filtering=ON).

In (d), (d') and (e) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)n- linker, —(CH$_2$CH$_2$O)n- linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plurality of conjugates is not particularly limited, as long as it is two or more, and the plurality can be, for example, 2, 3 or 4. Each of the nucleotides in (a) to (d), (a') to (d') and (e) above, whether identical or different, can be a nucleotide comprising a hydroxyl group at the 2' position of ribose or a nucleotide substituted by any groups (e.g., hydrogen atom, fluorine atom or —O-Me group) at the 2' position of ribose (e.g., ribose of pyrimidine nucleotide).

The aptamer of the present invention may be one wherein a sugar residue (e.g., ribose) of each nucleotide has been modified to increase the chymase binding activity, stability, drug deliverability and the like. As examples of the site to be modified in a sugar residue, one having the oxygen atom at the 2'-position, 3'-position and/or 4'-position of the sugar residue replaced with another atom, and the like can be mentioned. As examples of the modification, fluorination, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see, for example, Sproat et al., (1991) Nucle. Acid. Res. 19, 733-738; Cotton et al., (1991) Nucl. Acid. Res. 19, 2629-2635; Hobbs et al., (1973) Biochemistry 12, 5138-5145).

In the aptamer of the present invention, the common sequence or the structure represented by the formula (1)

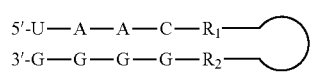

(1)

of the present invention may be modified as mentioned above. However, the second G of the GGGG part in UAACR$_1$N$_1$R$_2$GGGG is desirably free of O-methylation (modification with O-methyl) at the 2'-position of the sugar residue. Therefore, the aptamer of the present invention may be an aptamer in which the second G of the GGGG part in UAACR$_1$N$_1$R$_2$GGGG and the structure of the formula (1)

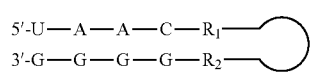

(1)

is free of O-methylation (modification with O-methyl). In this case, the second G of the GGGG part is preferably modified with a fluorine atom (fluorinated).

The aptamer of the present invention may also have a nucleic acid base (e.g., purine or pyrimidine) altered (e.g., chemical substitution) to increase the chymase binding activity and the like. As examples of such alterations, 5-position pyrimidine alteration, 6- and/or 8-position purine alteration, alteration with an extracyclic amine, substitution with 4-thiouridine, and substitution with 5-bromo or 5-iodo-uracil, and substitution with 8-(propyl)phenyl-rA (n-bz)-2'-tBDMS amidite can be mentioned.

The phosphate group contained in the aptamer of the present invention may be altered to confer resistance to nuclease and hydrolysis. For example, the P(O)O group may be substituted with P(O)S (thioate), P(S)S (dithioate), P(O)NR$_2$ (amidate), P(O)CH$_3$, P(O)BH$_3$, P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)].

The joining group is, for example, —O—, —N— or —S—, and nucleotides can bind to an adjoining nucleotide via these joining groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamer of the present invention can be synthesized as disclosed herein and by a method known per se in the art. A method of synthesis employs RNA polymerase. A DNA having a desired sequence and a promoter sequence of RNA polymerase is chemically synthesized, which, as a template, is transcribed by a publicly known method to obtain the desired RNA. The aptamer of the present invention can also be synthesized using DNA polymerase. A DNA having a desired sequence is chemically synthesized, which, as a template, is amplified by a method of public knowledge known as the polymerase chain reaction (PCR). This is rendered single-stranded by a publicly known method of polyacrylamide electrophoresis or enzyme treatment. When synthesizing a modified aptamer, elongation reaction efficiency can be increased by using a polymerase mutated at a particular site. The aptamer thus obtained can easily be purified by a publicly known method.

An aptamer can be synthesized in large amounts by chemical synthetic methods such as the amidite method and the phosphoramidite method. These synthetic methods are well known, as described in Nucleic Acid (Vol. 2) [1] Synthesis and Analysis of Nucleic Acid (edited by Yukio Sugiura, published by Hirokawa Publishing Company) and the like. Practically, a synthesizer such as OligoPilot100 or OligoProcess (manufactured by GE Healthcare Bioscience) is used. The aptamer thus synthesized can be purified by a method known per se such as chromatography.

Provided that an active group such as an amino group is introduced to an aptamer during the process of chemical synthesis by the phosphoramidite method or the like, a functional substance can be added after the synthesis. For example, by introducing an amino group to an end of the aptamer, it is possible to condense a polyethylene glycol chain incorporating a carboxyl group.

An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change widely.

An aptamer can be prepared by utilizing the SELEX method or an improved version thereof (for example, Ellington et al., (1990) Nature, 346, 818-822; Tuerk et al., (1990) Science, 249, 505-510). In the SELEX method, by rendering the selection criteria more rigorous by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target molecule, but this does not mean inhibiting a bioactivity of the target molecule. Chymase is a basic protein to which nucleic acids are thought to be likely to bind non-specifically, but aptamers other than those that bind strongly to a particular site of chymase do not influence the activity of the target molecule. In fact, the RNA comprising a random sequence used as a negative control did not inhibit the enzyme activity of chymase, although it bound to chymase weakly.

Based on an active aptamer thus selected, SELEX can be performed to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a pharmaceutical as it is. Hence, it is necessary to repeat try-and-error efforts to shorten the aptamer to a length of about 50 nucleotides or less enabling easy chemical synthesis. Depending on the primer design for an aptamer obtained by SELEX, the ease of the subsequent minimization operation changes. Unless the primer is designed successfully, subsequent development will be impossible even if an aptamer with activity is selected by SELEX. In the present invention, an aptamer retaining activity even with 28 nucleotides was obtained.

Aptamers are easily modifiable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the aptamer obtained with the target molecule is identified by repeated try-and-error efforts as described above, the activity remains unchanged in many cases even when a new sequence is added to both ends of the sequence. The length of the new sequence is not particularly limited.

Those of ordinary skill in the art can make a wide range of design or alterations of modifications, like sequences.

As stated above, aptamers permit a wide range of design or alterations of modifications. The present invention also provides a production method of aptamer that enables a wide range of design or alteration of an aptamer comprising a specified sequence (e.g., a sequence corresponding to a portion selected from among stem regions, internal loop regions, bulge regions, hairpin loop regions and single-strand regions: hereinafter, abbreviated as fixed sequence as required).

For example, the production method of such aptamer includes production of an aptamer comprising a fixed sequence by using a single kind of nucleic acid molecule or a plurality of kinds of nucleic acid molecules (e.g., a library of nucleic acid molecules with different numbers for "a" or "b") consisting of a nucleotide sequence shown by the formula:

| Primer sequence (i) | -(N)a-fixed sequence-(N)b- | Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a pharmaceutical or a diagnostic reagent, a test reagent or a reagents.

The aptamer and complex of the present invention can possess an activity of inhibiting a function of chymase. As stated above, chymase is profoundly associated with fibrosis and cardiovascular diseases. Therefore, the aptamer and complex of the present invention are useful as pharmaceuticals for treating or preventing diseases accompanied by fibrosis or cardiovascular disorders, as well as fibrosis and cardiovascular diseases.

The aptamer and complex of the present invention are capable of binding specifically to chymase. Therefore, the aptamer and complex of the present invention are useful as probes for chymase detection. The probes are useful in in vivo imaging of chymase, measurements of blood concentrations of chymase, tissue staining, ELISA and the like. The probes are also useful as diagnostic reagents, testing reagents, analytical reagents and the like for diseases involved by chymase (fibrosis, cardiovascular disorders, diseases accompanied by fibrosis or cardiovascular disorders, and the like).

Based on their specific binding to chymase, the aptamer and complex of the present invention can be used as ligands for purification of chymase.

The aptamer and complex of the present invention can be used as drug delivery vehicles.

Fibrosis is a disease caused by the progression of fibrosis of an organ or tissue for some reason, resulting in a decrease in the function of the organ or tissue. Therefore, fibrosis in a broad sense can be said a disease involving fibrosis of an organ or tissue.

Diseases involved by organ or tissue fibrosis include pulmonary fibrosis, prostatic hyperplasia, myocardial fibrosis, musculoskeletal fibrosis, myelofibrosis, hysteromyoma, scleroderma, adhesion after surgical operations, postoperative scars, burn scars, hypertrophic scars, keloid, atopic dermatitis, peritoneal sclerosis, asthma, liver cirrhosis, chronic pancreatitis, scirrhous gastric cancer, liver fibrosis, renal fibrosis, fibrous vascular diseases, retinitis due to fibrous microvasculitis as a diabetic complication, neurosis, nephropathies, glomerulonephritis, tubulointerstitial nephritis, hereditary renal diseases, arteriosclerotic peripheral arteritis and the like. In addition, colitis, osteoporosis, allergic conjunctivitis, fulminant hepatitis, skin vasculitis, urticaria pigmentosa, pruritus, dermatitis herpetiformis, bullous pemphigoid, psoriasis, esophagitis, achalasia, airway inflammation, atherosclerosis, varicose vein and the like can also be mentioned.

Cardiovascular diseases include angiopathies, aortic aneurysms, renal insufficiency, hypertension, arteriosclerosis, myocardial infarction, cardiac hypertrophy, heart failure, re-stenosis after angiopathies due to percutaneous transluminal coronary angioplasty and the like, diabetic and non-diabetic nephropathies, peripheral circulatory disorders and the like. In addition, pulmonary hypertension, aortic stenosis and the like can also be mentioned.

Chymase possesses enzyme activity and cleaves bioactive substances that can serve as substrates. Examples of substrates known to date include AngI, latent TGF-β, SCF, procollagen, procollagenase, pro-MMP-9, IL-1β precursor and the like. Chymase exhibits biological actions, via reactions for production or degradation of these bioactive peptides, including extracellular matrix remodeling, networks with cytokines, immunity, and vasoconstriction. Meanwhile, chymase itself acts to activate mast cells and to promote histamine release, and is closely associated with inflammation. Therefore, the aptamer and complex of the present invention are not limited to the above-described substrates, and can be used as pharmaceuticals or diagnostic reagents, testing reagents, and analytical reagents for diseases related to biological functions mediated by substrates accepted by chymase and diseases involved by chymase itself.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

There is no limitation on the route of administration of the pharmaceutical of the present invention, which can be administered by, for example, oral administration and parenteral administration.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant; C10, which promotes the absorption of water-soluble substances, and the like.

The pharmaceutical of the present invention can be coated by a method known per se for the purpose of taste masking, enteric dissolution, sustained release and the like as required. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., red iron oxide, titanium dioxide and the like) and the like are used. The pharmaceutical may be a rapid-release preparation or sustained-release preparation.

As preparations suitable for parenteral administration (for example, intravenous administration, subcutaneous administration, intramuscular administration, topical administration, intraperitoneal administration, intranasal administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use.

Sustained-release preparations are also suitable preparations. Dosage forms of sustained-release preparations include sustained release from carriers or containers embedded in the body, such as artificial bones, biodegradable bases or non-biodegradable sponges, bags and the like. Devices for continuous or intermittent, systemic or topical delivery from outside the body, such as drug pumps and osmotic pressure pumps, are also included in the scope of sustained-release preparations. Biodegradable bases include liposome, cationic liposome, Poly(lactic-co-glycolic) acid (PLGA), atherocollagen, gelatin, hydroxyapatite, polysaccharide sizofiran.

In addition to liquid injections, suspensions and sustained-release preparations, inhalants suitable for transpulmonary administration, ointments suitable for percutaneous administration, and the like are acceptable.

In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required. An inhalant can be produced according to a conventional method. Specifically, an inhalant can be produced by powdering or liquefying the aptamer or complex of the present invention, blending it in an inhalation propellant and/or carrier, and filling it in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as gaseous nitrogen and gaseous carbon dioxide and the like can be mentioned.

Here, as examples of the surfactant, oleic acid, lecithin, diethyleneglycol dioleate, tetrahydroflufuryl oleate, ethyl oleate, isopropyl myristate, glyceryl trioleate, glyceryl monolaurate, glyceryl monoleate, glyceryl monostearate, glyceryl monolysinoate, cetyl alcohol, stearyl alcohol, polyethyleneglycol 400, cetylpyridinium chloride, sorbitan trioleate (trade name Span 85), sorbitan monoleate (trade name Span 80), sorbitan monolaurate (trade name Span 20), polyoxyethylene hardened castor oil (trade name HCO-60), polyoxyethylene (20) sorbitan monolaurate (trade name Tween 20), polyoxyethylene (20) sorbitan monoleate (trade name Tween 80), lecithin of natural resource origin (trade name EPICLON), oleylpolyoxyethylene (2) ether (trade name Brij 92), stearyl polyoxyethylene (2) ether (trade name Brij 72), lauryl polyoxyethylene (4) ether (trade name Brij 30), oleylpolyoxyethylene (2) ether (trade name Genapol 0-020), block copolymer of oxyethylene and oxypropylene (trade name Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an aptamer of the present invention, which is the active ingredient, and used as a preparation.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and/or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying chymase.

The aptamer and/or the complex of the present invention can be immobilized onto a solid phase carrier by a method known per se. For example, a method that introduces an affinity substance (e.g., those described above) or a predetermined functional group into the aptamer and/or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating chymase. In particular, the present invention makes it possible to separate chymase from the proteins of other family proteins. The method of purification and concentration of the present invention can comprise adsorbing chymase to the solid phase carrier of the present invention, and eluting the adsorbed chymase with an eluent. Adsorption of chymase to the solid phase carrier of the present invention can be achieved by a method known per se. For example, a chymase-containing sample (e.g., bacterial or cell culture or culture supernatant, blood) is introduced into the solid phase carrier of the present invention or a composition containing the same. Chymase can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, urea, a chelating agent (e.g., EDTA), a sodium salt (e.g., NaCl), a potassium salt (e.g., KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after chymase adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The present invention also provides a method of detecting and quantifying chymase. In particular, the present invention makes it possible to detect and quantify chymase separately from the proteins of other family proteins. The method of detection and quantitation of the present invention can comprise measuring chymase by utilizing the aptamer of the present invention (e.g., by the use of the complex and solid phase carrier of the present invention). The method of detecting and quantifying chymase can be performed in the same manner as an immunological method, except that the aptamer of the present invention is used in place of an antibody. Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique, immunohistochemical staining method, and cell sorting method, detection and quantitation can be performed. The aptamer of the present invention can also be used as a molecular probe for PET and the like. These methods can be useful in, for example, measuring chymase contents in living organisms or biological samples, and in diagnosing a disease associated with chymase.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1: Preparation of RNA Aptamers that Bind Specifically to Chymase (1)

RNA aptamers that bind specifically to chymase were prepared using the SELEX method. SELEX was performed with improvements of the method of Ellington et al. (Ellington and Szostak, Nature 346, 818-822, 1990) and the method of Tuerk et al. (Tuerk and Gold, Science 249, 505-510, 1990). Chymase (Human Skin, manufactured by Calbiochem) immobilized on NHS-activated Sepharose 4 Fast Flow (manufactured by GE Healthcare) carrier was used as a target molecule. Chymase immobilization to the carrier was performed as directed in the specifications by GE Healthcare. The amount immobilized was confirmed by examining the chymase solution before immobilization and the supernatant just after immobilization by SDS-PAGE. As a result of the SDS-PAGE, no band of chymase was detected in the supernatant; it was confirmed that nearly all of the chymase used had been coupled. This means that about 167 pmol of chymase was immobilized to about 3 μL of the resin.

The RNA used in the first round (30N) was obtained by transcribing a chemically synthesized DNA using the DuraScribe™ T7 Transcription Kit (manufactured by Epicentre). The RNA obtained by this method has the 2'-position of ribose of the pyrimidine nucleotide fluoro-substituted. The following DNA of 72 nucleotides long, having a primer sequence at each end of a 30-nucleotide random sequence, was used as a DNA template. The DNA template and primers used were prepared by chemical synthesis.

```
DNA template:
                                    (SEQ ID NO: 34)
5'-TCACACTAGCACGCATAGGNNNNNNNNNNNNNNNNNNNNNNNN

NNNNNNCATCTGACCTCTCTCCTGCTCCC-3' primer Fwd:
                                    (SEQ ID NO: 35)
5'-TAATACGACTCACTATAGGGAGCAGGAGAGAGGTCAGATG-3'
``` primer Rev:

(SEQ ID NO: 36)
5'-TCACACTAGCACGCATAGG-3'

The sequential Ns in the DNA template (SEQ ID NO: 34) are 30 nucleotides in any combinations (30N: each N is A, G, C or T), producing a sequence region unique to each aptamer obtained. The primer Fwd comprises a promoter sequence of T7 RNA polymerase. The variation of the RNA pool used in the first round was theoretically $10^{14}$.

The RNA pool was added to the chymase-immobilized carrier, and allowed to stand at room temperature for 30 minutes. Then, to remove the RNA not bound to chymase, the resin was washed with solution A. Here, the solution A was a mixed solution of 145 mM sodium chloride, 5.4 mM potassium chloride, 1.8 mM calcium chloride, 0.8 mM magnesium chloride, and 20 mM Tris. The RNA bound to chymase was heated at 95° C. for 10 minutes with the addition of solution B as an eluent, and recovered from the supernatant. Here, the solution B was a mixture of 7M Urea, 3 mM EDTA, and 100 mM Tris-HCl (pH 6.6). The recovered RNA was amplified by RT-PCR and transcribed using the DuraScribe™ T7 Transcription Kit, and this was used as the pool for the next round. With this procedure taken as 1 round, the same operation was performed plural times. After completion of SELEX, the PCR product was cloned into pGEM-T Easy vector (manufactured by Promega), and the *Escherichia coli* strain DH5α (manufactured by Toyobo) was transformed therewith. After the plasmid was extracted from a single colony, the base sequences of clones were determined using a DNA sequencer (3130xl Genetic Analyzer, manufactured by ABI).

After 9 rounds of SELEX, the sequences of 56 clones were sequenced; sequence convergence was seen. The sequences of some of the clones are shown by SEQ ID NO: 1-6. These sequences contain the common sequence shown below:

$$UAACR_1N_1R_2GGGG$$

The aforementioned common sequence was present in 7 out of 56 clones. The secondary structures of these sequences were predicted using the MFOLD program (M. Zuker, Nucleic Acids Res. 31(13), 3406-3415, 2003). As a result, the part formed by the aforementioned common sequences $UAACR_1$ and $R_2GGGG$ was a very similar stem structure, and the part formed by N sandwiched thereby was a very similar loop structure. The predicted secondary structures of the aptamers of the sequences shown by SEQ ID NO: 1-6 are shown in FIG. 1. It is clear that the aforementioned common sequence takes a stem-loop structure represented by the following formula (1)

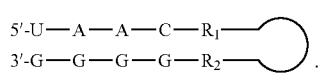
(1)

The stem-loop structure is surrounded by a square (□).

Given below are the respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 1
GGGAGCAGGAGAGAGGUCAGAUGAGCAUGCUUUUUGGUAACCGAUA

AUGGGGGCCUAUGCGUGCUAGUGUGA

SEQ ID NO: 2
GGGAGCAGGAGAGAGGUCAGAUGAUCGGACAUAACAUUGUUGGGGU

GUCAAGGCCUAUGCGUGCUAGUGUGA

SEQ ID NO: 3
GGGAGCAGGAGAGAGGUCAGAUGAUAACCAGUUGGGGGGUCAAUUA

CAUGGGACCUAUGCGUGCUAGUGUGA

SEQ ID NO: 4
GGGAGCAGGAGAGAGGUCAGAUGUAACUCUAUUGAGGGGCAUCAGC

ACAGUAGCCUAUGCGUGCUAGUGUGA

SEQ ID NO: 5
GGGAGCAGGAGAGAGGUCAGAUGAUGACCGAUUAUAGGUAACCACU

UAGGGGGCCUAUGCGUGCUAGUGUGA

SEQ ID NO: 6
GGGAGCAGGAGAGAGGUCAGAUGUCAUGACUUAUAGGUAACCGAUA

AUGGGGGCCUAUGCGUGCUAGUGUGA

[Common sequence]
$UAACR_1N_1R_2GGGG$

Figure 2:
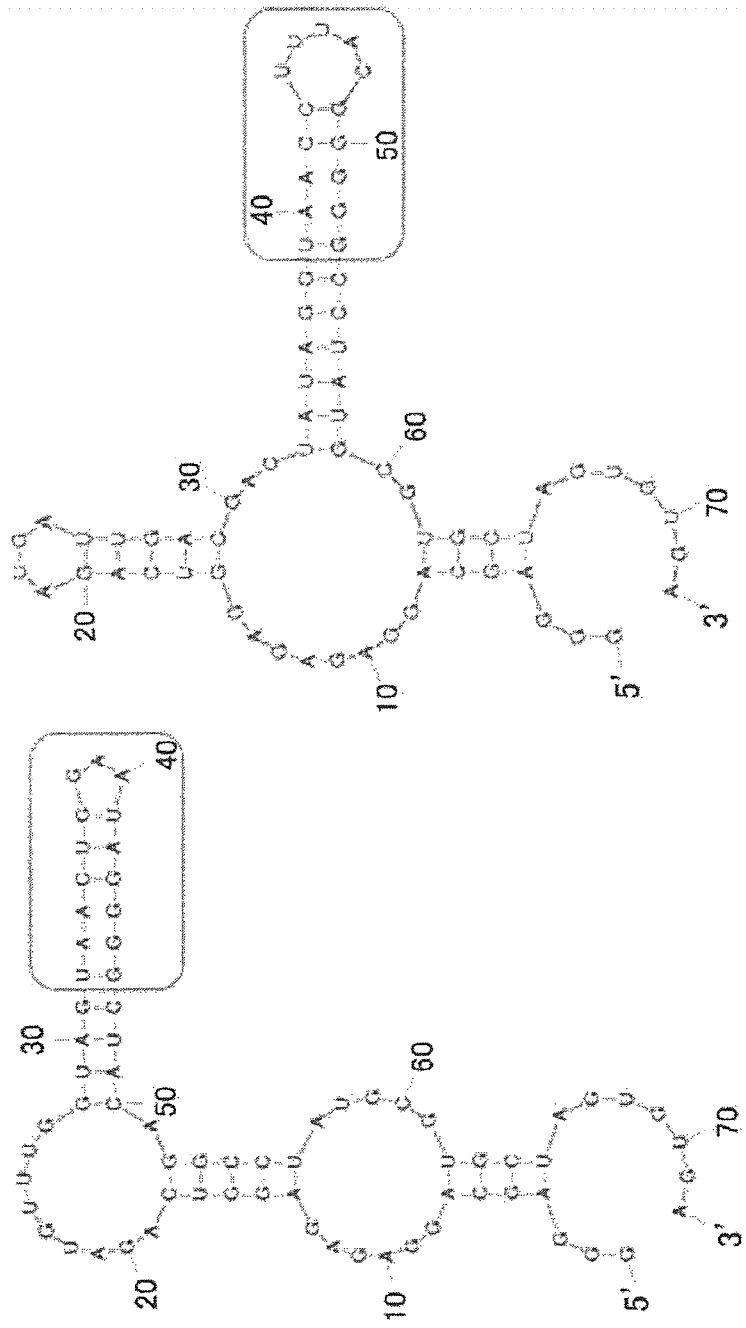
FIG. 2 shows the predicted secondary structures of the aptamers of the sequences shown by SEQ ID NO: 7-8.

The above-mentioned SELEX performed up to 9 rounds was continued under similar conditions, and the sequences of 8 clones at 10 rounds, 47 clones at 11 rounds, total 55 clones, were examined. The sequences of a part of the clones are shown in SEQ ID NO: 7-8. These sequences contained common sequences similar to that at 9 rounds. The common sequences were contained in 3 clones in 55 clones. The predicted secondary structures of the aptamers of the sequences shown by SEQ ID NO: 7-8 are shown in FIG. 2. The stem-loop structure is surrounded by a square (□). They all have a characteristic stem-loop structure as in FIG. 1.

Given below are respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 7
GGGAGCAGGAGAGAGGUCAGAUGUUUGGUAGUAACUGGAAUAGGGG

CUACAGGCCUAUGCGUGCUAGUGUGA

SEQ ID NO: 8
GGGAGCAGGAGAGAGGUCAGAUGAUUGACGACUAUAGGUAACCUUU

ACGGGGGCCUAUGCGUGCUAGUGUGA

Whether the nucleic acids shown by SEQ ID NO: 1-8 inhibit the enzyme activity of chymase was determined as described below. The chymase substrate used was Suc-Ala-Ala-Pro-Phe-MCA (manufactured by Peptide Institute, Inc.), which contains the 4-amino-acid peptide Ala-Ala-Pro-Phe, a standard substrate for chymotrypsin-like proteases. Here, Suc is a protecting succinyl group, and MCA is a 4-methylcoumaryl-7-amide group; upon cleavage of the C-terminal side of phenylalanine, AMC (7-amino-4-methylcoumarine) is released. By detecting the fluorescence of this AMC, the enzyme activity of chymase can be determined. The assay was performed using a 96-well plate (F16 Black Maxisorp Fluoronunc, manufactured by Nunc), with a reaction mixture volume of 100 µL, in solution C as a buffer solution. Here, the solution C is a mixed solution of 145 mM sodium chloride, 5.4 mM potassium chloride, 1.8 mM calcium chloride, 0.8 mM magnesium chloride, 20 mM Tris (pH 7.6), and 0.05% Tween20. First, nucleic acid was serially diluted in solution C to obtain 50 µL solutions. After 10 µL of the 1 mM substrate prepared in solution C was added thereto, the plate was set to the microplate reader SpectraMax190 (manufactured by Molecular Devices Corporation), and incubated at 37° C. for 5 minutes. Separately, 0.05 µg of chymase (recombinant, manufactured by SIGMA) was diluted in solution C to obtain a 40 µL chymase solution, and incubated at 37° C. for 5 minutes. The chymase solution was added to the mixture of the nucleic acid and substrate to initiate an enzyme reaction. The final chymase concentration in the reaction mixture was 16.7 nM, the final substrate concentration being 100 µM. The plate containing the reaction mixture was set to the microplate reader SpectraMax190 (manufactured by Molecular Devices Corporation), and examined for time-dependent changes in the fluorescence intensity at 37° C. for 5 minutes (or 30 minutes) (excitation wavelength 380 nm, detection wavelength 460 nm). A linear approximation of the increase in the fluorescence of the AMC released from the substrate by chymase activity was generated, and its slope was taken as the initial velocity ($V_{max}$). For control, samples were treated and analyzed in the same manner in two cases: use of a 30N (a nucleotide of 30 consecutive bases represented by N; N is A, G, C or T) nucleic acid pool (negative control), and use of chymostatin, a known chymotrypsin-like serine protease inhibitor (positive control). Taking the initial reaction velocity without the nucleic acid and inhibitor ($V_0$) as a 100% enzyme activity, the inhibitory rate of each test substance was calculated using the following equation:

Inhibitory rate (%)=$(1-V_{max}/V_0) \times 100$

The inhibitor concentration required to cause a 50% inhibition of the enzyme activity ($IC_{50}$) was determined. The results are shown in Table 1. ">0.5" indicates that no inhibitory activity was observed in the concentration range up to 0.5 µM. Each $IC_{50}$ value is a mean of 2 or 3 measurements.

TABLE 1

| SEQ ID NO: | length | IC50 [µM] |
| --- | --- | --- |
| 1 | 72 | 0.0410 |
| 2 | 72 | 0.0310 |
| 3 | 72 | 0.0260 |
| 4 | 72 | 0.0108 |
| 5 | 72 | 0.0070 |
| 6 | 72 | 0.0055 |
| 7 | 72 | 0.0520 |
| 8 | 72 | 0.0350 |

The negative control 30N did not exhibit inhibitory activity ($IC_{50}$>0.5 µM). The positive control chymostatin exhibited $IC_{50}$ values of 0.1 µM-0.2 µM.

In summary, the aptamers containing the common sequence and listed in Table 1 exhibited inhibitory activity against chymase. The aptamers exhibiting $IC_{50}$ values of 0.1 µM or less, in particular, can be judged to have an excellent inhibitory effect. These findings demonstrate that the combination of $R_1$ and $R_2$ contained in these common sequences may be any of A/U, C/G, A/C and G/U.

SELEX was performed in the same manner as above, but using a template whose random sequence was of 30 nucleotides, and a primer sequence different from that used in the above-mentioned SELEX. Chymase (recombinant, manufactured by SIGMA) immobilized on NHS-activated Sepharose 4 Fast Flow (manufactured by GE Healthcare) carrier was used as a target substance. The sequences of the template and primers used are shown below. The DNA template and primers were chemically synthesized.

```
DNA template:
                                    (SEQ ID NO: 37)
5'-TCTGTCCTCAGTACTTGANNNNNNNNNNNNNNNNNNNNNNNNNN

NNNNNNNNNNNNNNNNNNGTCTGTCGCTTCGTTCCC-3' primer Fwd:
                                    (SEQ ID NO: 38)
5'-TAATACGACTCACTATAGGGAACGAAGCGACAGAC-3' primer Rev:
                                    (SEQ ID NO: 39)
5'-TCTGTCCTCAGTACTTGA-3'
```

The sequential Ns in the DNA template (SEQ ID NO: 37) are 40 nucleotides in any combinations (40N: each N is A, G, C or T), producing a sequence region unique to each aptamer obtained. The primer Fwd comprises a promoter sequence of T7 RNA polymerase. The variation of the RNA pool used in the first round was theoretically $10^{14}$.

The RNA pool was added to the chymase-immobilized carrier, and allowed to stand at room temperature for 30 minutes. Then, to remove the RNA not bound to chymase, the resin was washed with solution A. Here, the solution A was a mixed solution of 145 mM sodium chloride, 5.4 mM potassium chloride, 1.8 mM calcium chloride, 0.8 mM magnesium chloride, and 20 mM Tris. The RNA bound to chymase was heated at 95° C. for 10 minutes with the addition of solution B as an eluent, and recovered from the supernatant. Here, the solution B was a mixture of 7M Urea, 3 mM EDTA, and 100 mM Tris-HCl (pH 6.6). The recovered RNA was amplified by RT-PCR and transcribed using the DuraScribe™ T7 Transcription Kit, and this was used as the pool for the next round. With this procedure taken as 1 round, the same operation was performed plural times. After completion of SELEX, the PCR product was cloned into pGEM-T Easy vector (manufactured by Promega), and the *Escherichia coli* strain DH5α (manufactured by Toyobo) was transformed therewith. After the plasmid was extracted from a single colony, the base sequences of clones were determined using a DNA sequencer (3130xl Genetic Analyzer, manufactured by ABI).

Figure 3:
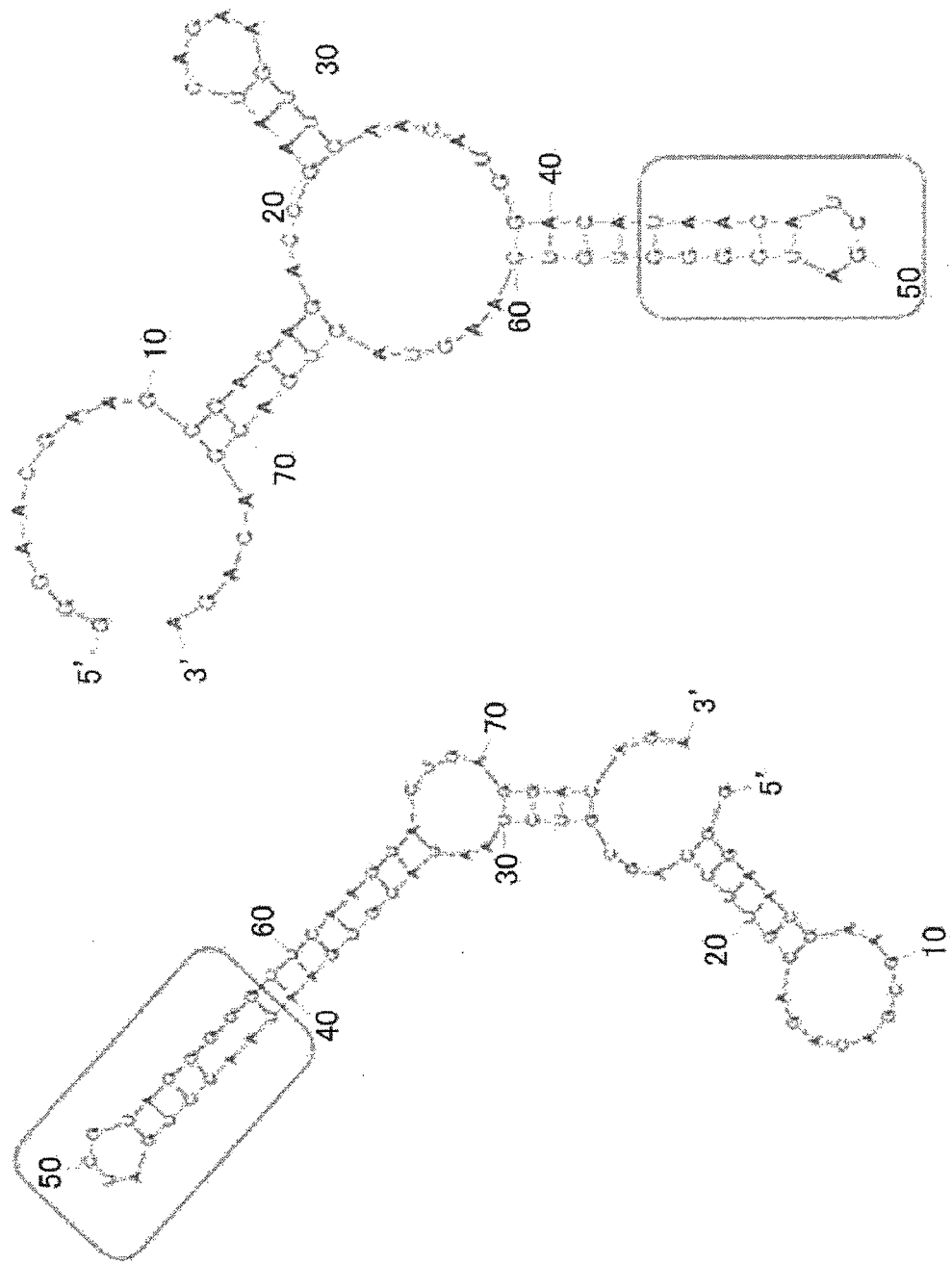
FIG. 3 shows the predicted secondary structures of the aptamers of the sequences shown by SEQ ID NO: 9-10.

After 8 rounds of SELEX, the sequences of 38 clones were sequenced; sequence convergence was seen. The sequences of some of the clones are shown by SEQ ID NO: 9-10. Among them, two sequences were present that are shown by SEQ ID NO: 10. The common sequence was present in 3 out of the 38 clones. The secondary structures of these sequences were predicted using the MFOLD program (M. Zuker, Nucleic Acids Res. 31(13), 3406-3415, 2003); the portions formed by the common sequence portion had a similar loop structure. The predicted secondary structures of the aptamers of the sequences shown by SEQ ID NO: 9-10 are shown in FIG. 3. The stem-loop structure is surrounded by a square (□).

Given below are the respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 9
GGGAACGAAGCGACAGACGUUCCAGCGUCUAAUACGUGAAUAACCU

GAUCGUAGGGGUUCAAGUACUGAGGACAGA

SEQ ID NO: 10
GGGAACGAAGCGACAGACCGAAUCAGAAGUUCAACAUGGACAUAAC

AUCGAUGGGGUGUCAAGUACUGACGACAGA

Whether the nucleic acids shown by SEQ ID NO: 9 and 10 inhibit the enzyme activity of chymase was determined by the following method. Angiotensin I is converted by chymase to angiotensin II, during which a peptide fragment His-Leu is released. Since the peptide His-Leu is fluorescently derivatized by o-phthalaldehyde, its fluorescence intensity can be quantitatively measured.

The total volume of solution for an enzyme reaction in the assay was set to 50 µL, and the reaction was performed in solution C buffer. At first, native (manufactured by Calbiochem) was diluted with solution C to give 5 µL thereof. Here, the native is chymase purified from human skin mast cell. The nucleic acid was serially diluted with solution C at a concentration of 0.0027-2 µM to give 25 µL thereof. The chymase solution (5 µL) and the nucleic acid solution (25 µL) were mixed, and the mixture was incubated at 37° C. for 5 min. On the other hand, 125 mM angiotensin I (manufactured by PEPTIDE INSTITUTE, INC.) was prepared in solution C to give 20 µL thereof, which was incubated at 37° C. for 5 min. The angiotensin I solution was added to a mixture of chymase and nucleic acid to start an enzyme reaction. The final chymase concentration of the reaction solution was 0.5 nM, and the final substrate concentration was 50 µM. After reaction at 37° C. for 90 min, ice-cooled 30% trichloroacetic acid solution (25 µL) was added to quench the reaction. The whole mixture was centrifuged at 4° C., 14000 rpm for 10 min, and the supernatant (30 µL) was used for the next fluorescence induction reaction.

The above-mentioned supernatant (30 µL) was added to a 96 well plate (black, manufactured by Costar), a solution (15 µL) of 2% o-phthalaldehyde (manufactured by SIGMA) in methanol and 0.3M NaOH solution (170 µL) were added to each well, and the mixture was incubated at room temperature for 10 min. Then, 3M HCl solution (25 µL) was added to quench the reaction. The plate was set on a microplate reader SpectraMax190 (manufactured by Molecular device) and the fluorescence intensity was measured at an excitation wavelength of 355 nm and a fluorescence wavelength of 460 nm.

The fluorescence intensity at reaction time 0 min under each condition was used as a blank. The fluorescence intensity detected by the addition of the same amount of solution C instead of the nucleic acid in the chymase enzyme reaction was taken as 100%, and the inhibitory rate of each test substance was calculated by the following formula.

Inhibitory rate (%)=[1−{(fluorescence intensity with test substance−fluorescence intensity of blank with test substance)/(fluorescence intensity without test substance−fluorescence intensity of blank without test substance)}]×100

The concentration of the inhibitor necessary for 50% inhibition of the enzyme activity ($IC_{50}$) was determined. The results are shown in Table 2. In the Table, the $IC_{50}$ value is a mean of 2 or 3 measurements.

TABLE 2

| SEQ ID NO: | length | IC50 [µM] |
|---|---|---|
| 9 | 77 | 0.00022 |
| 10 | 76 | 0.00043 |

The $IC_{50}$ value of the chymostatin used as a positive control is 0.35-0.5 µM, and any nucleic acid contained in Table 2 is expected as a drug for the prophylaxis and/or treatment of various diseases involving angiotensin, since it shows a strong chymase inhibitory activity even when angiotensin I, a native substrate, is used.

Example 2: Strand Shortening of Aptamer

Figure 4:
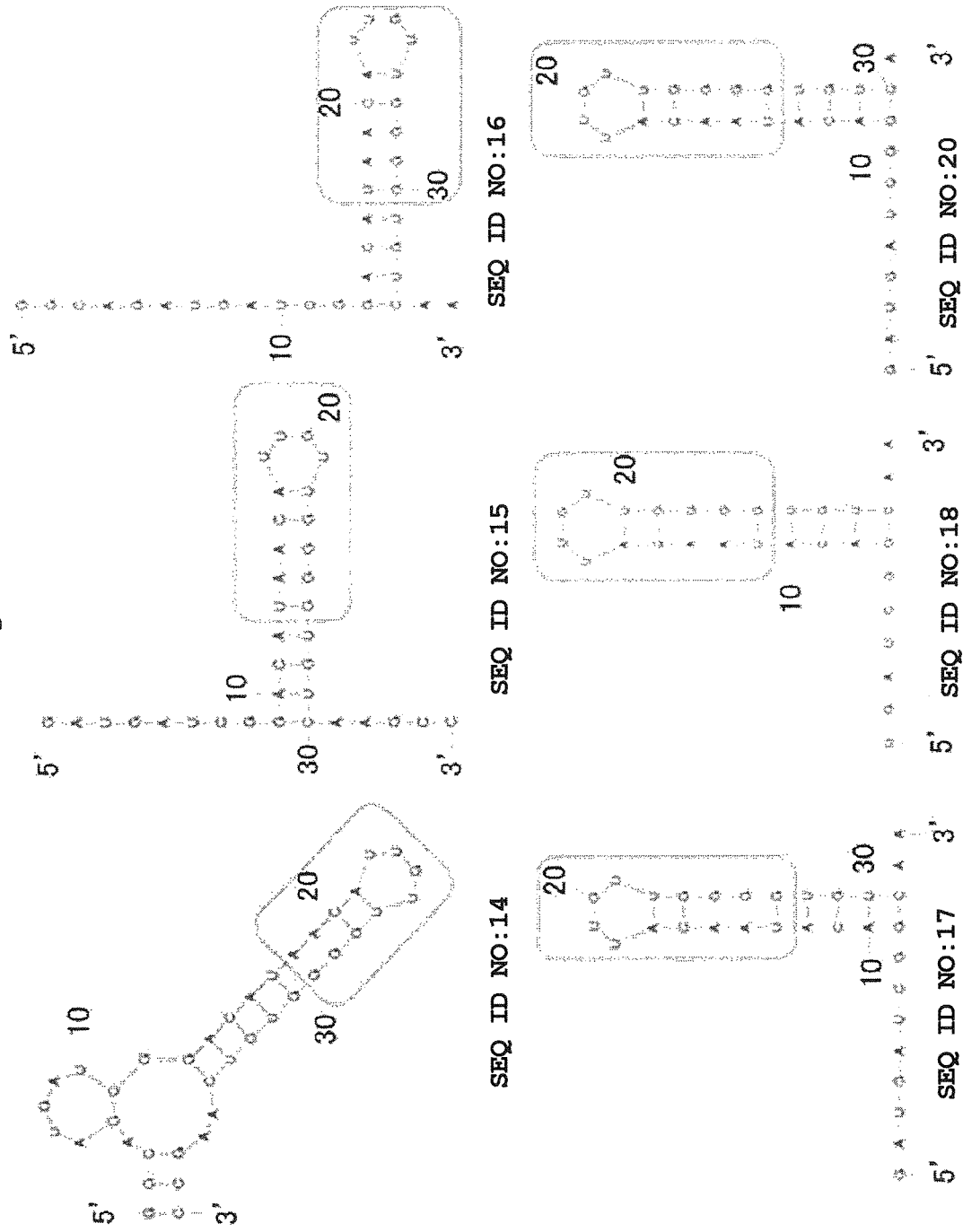
FIG. 4 shows the predicted secondary structures of the aptamers of the sequences shown by SEQ ID NO: 14-18, 20.

The aptamer shown by SEQ ID NO: 2 was shortened. The aptamer shown by SEQ ID NO: 2 contains the common sequence. The shortened sequences are shown in SEQ ID NO: 11-20. The predicted secondary structures of a part of the aptamers shown by SEQ ID NO: 11-20 are shown in FIG. 4. In FIG. 4, the common sequence is surrounded by a square (□).

Given below are the nucleotide sequences shown by SEQ ID NO: 11-20, respectively. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 11
(sequence obtained by shortening sequence shown by SEQ ID NO: 2 to length of 43 nucleotides containing common sequence)

GGGUCAGAUGAUCGGACAUAACAUUGUUGGGGUGUCAAGGCCC

SEQ ID NO: 12
(sequence obtained by shortening sequence shown by SEQ ID NO: 2 to length of 22 nucleotides containing common sequence)

GACAUAACAUUGUUGGGGUGUC

SEQ ID NO: 13
(sequence obtained by shortening sequence shown by SEQ ID NO: 2 to length of 27 nucleotides containing common sequence)

GGACAUAACAUUGUUGGGGUGUCAAGG

SEQ ID NO: 14
(sequence obtained by shortening sequence shown by SEQ ID NO: 2 to length of 39 nucleotides containing common sequence)

GGCAGAUGAUCGGACAUAACAUUGUUGGGGUGUCAAGCC

SEQ ID NO: 15
(sequence obtained by shortening sequence shown by SEQ ID NO: 2 to length of 35 nucleotides containing common sequence)

GAUGAUCGGACAUAACAUUGUUGGGGUGUCAAGCC

SEQ ID NO: 16
(sequence obtained by shortening sequence shown by SEQ ID NO: 2 to length of 36 nucleotides containing common sequence)

GGCAGAUGAUCGGACAUAACAUUGUUGGGGUGUCAA

SEQ ID NO: 17
(sequence obtained by shortening sequence shown by SEQ ID NO: 2 to length of 32 nucleotides containing common sequence)

GAUGAUCGGACAUAACAUUGUUGGGGUGUCAA

SEQ ID NO: 18
(sequence obtained by shortening sequence shown by SEQ ID NO: 2 to length of 30 nucleotides containing common sequence)

UGAUCGGACAUAACAUUGUUGGGGUGUCAA

SEQ ID NO: 19
(sequence obtained by shortening sequence shown by SEQ ID NO: 2 to length of 28 nucleotides containing common sequence)

AUCGGACAUAACAUUGUUGGGGUGUCAA

SEQ ID NO: 20
(sequence obtained by shortening sequence shown by SEQ ID NO: 2 to length of 31 nucleotides containing common sequence)

GAUGAUCGGACAUAACAUUGUUGGGGUGUCA

The nucleic acids of SEQ ID NO: 11-20 were all produced by chemical synthesis. In the evaluation of SEQ ID NO: 11-20, a method similar to the evaluation method of inhibitory activity against chymase shown in Example 1 by using angiotensin I as a substrate was used for measurement. The measurement results are shown in Table 3. In the Table, ">1" indicates that no inhibitory activity was observed in the concentration range up to 1 µM. The $IC_{50}$ value is a mean of 2 or 3 measurements.

TABLE 3

| SEQ ID NO: | length | IC50 [µM] |
|---|---|---|
| 2 | 72 | 0.0100 |
| 11 | 43 | 0.0547 |
| 12 | 22 | >1 |
| 13 | 27 | >1 |
| 14 | 39 | 0.0068 |
| 15 | 35 | 0.0014 |
| 16 | 36 | 0.0020 |
| 17 | 32 | 0.0014 |
| 18 | 30 | 0.0021 |
| 19 | 28 | 0.0144 |
| 20 | 31 | 0.0018 |

Many of the shortened forms of SEQ ID NO: 2 described in Table 3 exhibited inhibitory activity against chymase. The aptamers exhibiting $IC_{50}$ values of 0.01 µM or less, in particular, can be judged to have an excellent inhibitory effect. From the results of SEQ ID NO: 18, it was found that an aptamer shortened to 30 nucleotides containing the common sequence also maintained the activity. This demonstrates that the common sequence is critical to the binding and inhibitory activity against chymase.

Example 3: Alteration of Shortened Aptamer

To enhance nuclease resistance of the aptamer shown by SEQ ID NO: 17, an altered aptamer with terminal modification, an altered aptamer wherein the 2'-position of ribose of purine base in the sequence is modified with O-methyl group or F, and an altered aptamer wherein phosphorothioate is introduced were prepared. The sequences are shown by SEQ ID NO: 17(1)-17(25).

Given below are the respective nucleotide sequences. Unless otherwise stated, the following individual sequences are shown in the direction from 5' to 3', modification at the 2'-position of ribose is shown in the parenthesis, F is a fluorine atom, M is an O-methyl group, and PHE is 8-(propyl)phenyl-rA(n-bz)-2'-tBDMS amidite. In respective sequence terminals, idT shows modification with inverted-dT, and S shows modification with thiol group. X shows a peptide sequence by a peptide bond of the C-terminal of phenylalanine and the N-terminal of cysteine, and Y shows a peptide sequence by a peptide bond of the N-terminal of phenylalanine and the C-terminal of cysteine. In the sequences, s shows phosphorothioation of a phosphate group between the nucleotides. Z shows TC6F amidite.

SEQ ID NO: 17(1)
sequence obtained by introducing 2'-O-methyl modification into 5'-terminal and 3'-terminal, introducing 2'-O-methyl modification into the first G and the second G of the common sequence GGGG of the sequence shown by SEQ ID NO: 17

GAU(F)GAU(F)C(F)GGAC(F)AU(F)AAC (F)AU(F)U(F)GU(F)U(F)G(M)G(M)GGU (F)GU(F)C(F)AA

SEQ ID NO: 17(2)
sequence obtained by introducing idT modification into 5'-terminal and 3'-terminal, introducing 2'-O-methyl modification into 12 positions in the sequence other than the common sequence, and introducing 2'-O-methyl modification into G other than the second G in the common sequence GGGG, of the sequence shown by SEQ ID NO: 17 idT-G(M)A(M)U(F)G(M)A(M)U(F)C(F)G (M)G(M)A(M)C(F)A(M)U(F)AAC(F)AU(F)

U(F)G(M)U(F)U(F)G(M)GG(M)G(M)U (F)G(M)U(F)C(F)A(M)A(M)-idT

SEQ ID NO: 17(3)
sequence obtained by introducing idT modification into 5'-terminal and 3'-terminal, introducing 2'-O-methyl modification into 12 positions in the sequence other than the common sequence, and introducing 2'-O-methyl modification into G other than the first G in the common sequence GGGG, of the sequence shown by SEQ ID NO: 17

```
idT-G(M)A(M)U(F)G(M)A(M)U(F)C(F)G(M)G(M)A(M)

C(F)A(M)U(F)AAC(F)AU(F)U(F)G(M)U(F)U(F)GG(M)

G(M)G(M)U(F)G(M)U(F)C(F)A(M)A(M)-idT
```

SEQ ID NO: 17(4)

sequence obtained by introducing idT modification into 5'-terminal and 3'-terminal, introducing 2'-O-methyl modification into 12 positions in the sequence other than the common sequence, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)A(M)

C(F)A(M)U(F)AAC(F)ATTG(M)U(F)U(F)G(M)GG(M)

G(M)U(F)G(M)U(F)C(F)A(M)A(M)-idT
```

SEQ ID NO: 17(5)

sequence obtained by introducing idT modification into 5'-terminal and 3'-terminal, introducing 2'-O-methyl modification into 12 positions in the sequence other than the common sequence, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)A(M)

C(F)A(M)U(F)AAC(F)ATTG(M)U(F)U(F)G(M)GG(M)

G(M)TG(M)TCA(M)A(M)-idT
```

SEQ ID NO: 17(6)

sequence obtained by introducing idT modification into 5'-terminal and 3'-terminal, introducing 2'-O-methyl modification into 13 positions in the sequence other than the common sequence, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)

A(M)C(F)A(M)U(F)AAC(F)A(M)TTG(M)U(F)U(F)

G(M)GG(M)G(M)TG(M)TCA(M)A(M)-idT
```

SEQ ID NO: 17(7)

sequence obtained by introducing idT modification into 5'-terminal and 3'-terminal, introducing 2'-O-methyl modification into 13 positions in the sequence other than the common sequence, and introducing 2'-O-methyl modification into G other than the second G in the common sequence GGGG, of the sequence shown by SEQ ID NO: 17

```
idT-G(M)A(M)TG(M)A(M)U(F)C(F)G(M)G(M)

A(M)CA(M)LT(F)AAC(F)A(M)TTG(M)U(F)U(F)

G(M)GG(M)G(M)TG(M)TCA(M)A(M)-idT
```

SEQ ID NO: 17(8)

sequence obtained by introducing idT modification into 5'-terminal and 3'-terminal, introducing 2'-O-methyl modification into 13 positions in the sequence other than the common sequence, introducing 2'-O-methyl modification into U in the common sequence UAAC, and introducing 2'-O-methyl modification into G other than the second G in the common sequence GGGG, of the sequence shown by SEQ ID NO: 17

```
idT-
G(M)A(M)U(F)G(M)A(M)U(F)C(F)G(M)G(M)A(M)C(F)A(M)

U(M)AAC(F)A(M)TTG(M)U(F)U(F)G(M)GG(M)G(M)TG(M)

TCA(M)A(M)-idT
```

SEQ ID NO: 17(9)

sequence obtained by introducing idT modification into 5'-terminal and 3'-terminal, introducing 2'-O-methyl modification into 13 positions in the sequence other than the common sequence, introducing 2'-O-methyl modification into C in the common sequence UAAC, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)A(M)C(F)

A(M)U(F)AAC(M)A(M)TTG(M)U(F)U(F)G(M)GG(M)G(M)

TG(M)TCA(M)A(M)-idT
```

SEQ ID NO: 17(10)

sequence obtained by introducing idT modification into 5'-terminal and 3'-terminal, introducing 2'-O-methyl modification into 14 positions in the sequence other than the common sequence, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)A(M)C(F)

A(M)U(F)AAC(F)A(M)TTG(M)U(M)U(F)G(M)GG(M)G(M)

TG(M)TCA(M)A(M)-idT
```

SEQ ID NO: 17(11)

sequence obtained by introducing idT modification into 5'-terminal and 3'-terminal, introducing 2'-O-methyl modification into 14 positions in the sequence other than the common sequence, and introducing 2'-O-methyl modification into G other than the second G in the common sequence GGGG, of the sequence shown by SEQ ID NO: 17

```
idT-G(M)A(M)U(F)G(M)A(M)U(F)C(F)G(M)G(M)A(M)C(F)

A(M)U(F)AAC(F)A(M)TTG(M)U(F)U(M)G(M)GG(M)G(M)

TG(M)TCA(M)A(M)-idT
```

SEQ ID NO: 17(12)

sequence obtained by introducing modification of peptide sequence by peptide binding of C-terminal of phenylalanine and N-terminal of cysteine into 5'-terminal by thiol group, introducing idT modification into 3'-terminal, introducing 2'-O-methyl modification into 13 positions in the sequence other than the common sequence, and introducing 2'-O-methyl modification into G other than the second G in the common sequence GGGG, of the sequence shown by SEQ ID NO: 17

X-S-G(M)A(M)U(F)G(M)A(M)U(F)C(F)G(M)G(M)A(M)C(F)

A(M)U(F)AAC(F)A(M)TTG(M)U(F)U(F)G(M)GG(M)G(M)

TG(M)TCA(M)A(M)-idT

SEQ ID NO: 17(13)

sequence obtained by introducing modification of peptide sequence by peptide binding of N-terminal of phenylalanine and C-terminal of cysteine into 5'-terminal by thiol group, introducing idT modification into 3'-terminal, introducing 2'-O-methyl modification into 13 positions in the sequence other than the common sequence, and introducing 2'-O-methyl modification into G other than the second G in the common sequence GGGG, of the sequence shown by SEQ ID NO: 17

Y-S-G(M)A(M)U(F)G(M)A(M)U(F)C(F)G(M)G(M)A(M)C(F)

A(M)U(F)AAC(F)A(M)TTG(M)U(F)U(F)G(M)GG(M)G(M)

TG(M)TCA(M)A(M)-idT

SEQ ID NO: 17(14)

sequence obtained by introducing idT modification into 5'-terminal, introducing modification of peptide sequence by peptide binding of N-terminal of phenylalanine and C-terminal of cysteine into 3'-terminal by thiol group, introducing 2'-O-methyl modification into 13 positions in the sequence other than the common sequence, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)AAC(F)A(M)TTG(M)U(F)U(F)G(M)GG(M)G(M)

TG(M)TCA(M)A(M)-S-Y

SEQ ID NO: 17(15)

sequence obtained by introducing idT modification into 5'-terminal and 3'-terminal, introducing 2'-O-methyl modification into 12 positions and 8-(propyl)phenyl-rA(n-bz)-2'-tBDMS amidite modification into one position in the sequence other than the common sequence, and introducing 2'-O-methyl modification into G other than the second G in the common sequence GGGG, of the sequence shown by SEQ ID NO: 17 idT-G(M)A(PHE)U(F)G(M)A(M)U(F)C(F)G(M)G(M)A(M)

C(F)A(M)U(F)AAC(F)A(M)TTG(M)U(F)U(F)G(M)GG(M)

G(M)TG(M)TCA(M)A(M)-idT

SEQ ID NO: 17(16)

sequence obtained by introducing idT modification into 5'-terminal and 3'-terminal, introducing 2'-O-methyl modification into 12 positions and 8-(propyl)phenyl-rA(n-bz)-2'-tBDMS amidite modification into one position in the sequence other than the common sequence, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)AAC(F)A(M)TTG(M)U(F)U(F)G(M)GG(M)G(M)

TG(M)TCA(PHE)A(M)-idT

SEQ ID NO: 17(17)

sequence obtained by introducing idT modification into 5'-terminal and 3'-terminal, introducing 2'-O-methyl modification into 12 positions and 8-(propyl)phenyl-rA(n-bz)-2'-tBDMS amidite modification into one position in the sequence other than the common sequence, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)AAC(F)A(M)TTG(M)U(F)U(F)G(M)GG(M)G(M)

TG(M)TCA(M)A(PHE)-idT

SEQ ID NO: 17(18)

sequence obtained by introducing idT modification into 5'-terminal and 3'-terminal, introducing 2'-O-methyl modification into 13 positions in the sequence other than the common sequence, phosphorothioating phosphoric acid group binding U nucleotides in the common sequence UAAC, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)sAAC(F)A(M)TTG(M)U(F)U(F)G(M)GG(M)G(M)

TG(M)TCA(M)A(M)-idT

SEQ ID NO: 17(19)

sequence obtained by introducing idT modification into 5'-terminal and 3'-terminal, introducing 2'-O-methyl modification into 13 positions in the sequence other than the common sequence, phosphorothioating phosphoric acid group binding the first A nucleotides in the common sequence UAAC, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)AsAC(F)A(M)TTG(M)U(F)U(F)G(M)GG(M)G(M)

TG(M)TCA(M)A(M)-idT

SEQ ID NO: 17(20)

sequence obtained by introducing idT modification into 5'-terminal and 3'-terminal, introducing 2'-O-methyl modification into 13 positions in the sequence other than the common sequence, phosphorothioating phosphoric acid group binding the second A nucleotides in the common sequence UAAC, and introducing 2'-O-methyl modification into G other than the second G in the common sequence GGGG, of the sequence shown by SEQ ID NO: 17 idT-G(M)A(M)U(F)G(M)A(M)U(F)C(F)G(M)G(M)A(M)C(F)

A(M)U(F)AAsC(F)A(M)TTG(M)U(F)U(F)G(M)GG(M)G(M)

TG(M)TCA(M)A(M)-idT

SEQ ID NO: 17(21)

sequence obtained by introducing idT modification into 5'-terminal and 3'-terminal, introducing 2'-O-methyl modification into 13 positions in the sequence other than the common sequence, phosphorothioating phosphoric acid group binding the second A nucleotides in the common sequence UAAC, introducing 2'-O-methyl modification into G other than the second G in the common sequence GGGG, and phosphorothioating phosphoric acid group binding the second G nucleotides, of the sequence shown by SEQ ID NO: 17 idT-G(M)A(M)U(F)G(M)A(M)U(F)C(F)G(M)G(M)A(M)C(F)

A(M)U(F)AAC(F)A(M)TTG(M)U(F)U(F)G(M)GsG(M)G(M)

TG(M)TCA(M)A(M)-idT

SEQ ID NO: 17(22)

sequence obtained by introducing idT modification into 5'-terminal and 3'-terminal, introducing 2'-O-methyl modification into 19 positions and 8-(propyl)phenyl-rA(n-bz)-2'-tBDMS amidite modification into one position in the sequence other than the common sequence, introducing 2'-O-methyl modification into U and C of the common sequence UAAC, and introducing 2'-O-methyl modification into G other than the second G in the common sequence GGGG, of the sequence shown by SEQ ID NO: 17 idT-A(PHE)A(M)U(M)G(M)A(M)U(F)C(F)G(M)G(M)A(M)

C(M)A(M)U(M)AAC(M)A(M)U(M)U(M)G(M)U(M)U(M)G(M)

GG(M)G(M)TG(M)U(M)C(M)A(M)A(M)-idT

SEQ ID NO: 17(23)

sequence obtained by introducing idT modification into 5'-terminal and 3'-terminal, introducing 2'-O-methyl modification into 11 positions and 8-(propyl)phenyl-rA(n-bz)-2'-tBDMS amidite modification into one position in the sequence other than the common sequence, and introducing 2'-O-methyl modification into G other than the second G in the common sequence GGGG, of the sequence shown by SEQ ID NO: 17 idT-

G(M)A(PHE)U(F)G(M)A(M)U(F)C(F)G(M)G(M)A(M)C(F)A(M)

U(F)AAC(F)AU(F)U(F)G(M)U(F)U(F)G(M)GG(M)G(M)U(F)G (M)U(F)C(F)A(M)-idT

SEQ ID NO: 17(24)

sequence obtained by introducing TC6F amidite modification into 5'-terminal, introducing idT modification into 3'-terminal, introducing 2'-O-methyl modification into 20 positions in the sequence other than the common sequence, introducing 2'-O-methyl modification into U and C of the common sequence UAAC, and introducing 2'-O-methyl modification into G other than the second G in the common sequence GGGG, of the sequence shown by SEQ ID NO: 17 idT-

ZA(M)U(M)G(M)A(M)U(F)C(F)G(M)G(M)A(M)C(M)A(M)U(M)

AAC(M)A(M)U(M)U(M)G(M)U(M)U(M)G(M)GG(M)G(M)TG(M)U (M)C(M)A(M)A(M)-idT

SEQ ID NO: 17(25)

sequence obtained by introducing TC6F amidite modification into 5'-terminal, introducing idT modification into 3'-terminal, introducing 2'-O-methyl modification into 20 positions in the sequence other than the common sequence, introducing 2'-O-methyl modification into U and C of the common sequence UAAC, and introducing 2'-O-methyl modification into G other than the second G in the common sequence GGGG, of the sequence shown by SEQ ID NO: 17 idT-

ZA(M)U(M)G(M)A(M)U(F)C(F)G(M)G(M)A(M)C(M)A(M)U(M)

AAC(M)A(M)U(M)U(M)G(M)U(M)U(M)G(M)GG(M)G(M)TG(M)

U(M)C(M)A(M)A(M)-idT

All nucleic acids of SEQ ID NO: 17(1)-17(25) were prepared by chemical synthesis. In the evaluation of SEQ ID NO: 17(1)-17(25), a method similar to the evaluation method of inhibitory activity against chymase shown in Example 1 by using angiotensin I as a substrate was used for measurement. The measurement results are shown in Table 4. In the Table, the $IC_{50}$ value is a mean of 2 or 3 measurements.

TABLE 4

| SEQ ID NO: | length | IC50 [μM] |
| --- | --- | --- |
| 2 | 72 | 0.01000 |
| 17 | 32 | 0.00140 |
| 17(1) | 32 | 0.04436 |
| 17(2) | 32 | 0.00021 |
| 17(3) | 32 | 0.00566 |
| 17(4) | 32 | 0.00020 |
| 17(5) | 32 | 0.00017 |
| 17(6) | 32 | 0.00014 |
| 17(7) | 32 | 0.00017 |
| 17(8) | 32 | 0.00013 |
| 17(9) | 32 | 0.00016 |
| 17(10) | 32 | 0.00013 |
| 17(11) | 32 | 0.00014 |
| 17(12) | 32 | 0.00019 |
| 17(13) | 32 | 0.00016 |
| 17(14) | 32 | 0.00019 |
| 17(15) | 32 | 0.00013 |
| 17(16) | 32 | 0.00018 |
| 17(17) | 32 | 0.00019 |
| 17(18) | 32 | 0.00015 |
| 17(19) | 32 | 0.00019 |
| 17(20) | 32 | 0.00018 |
| 17(21) | 32 | 0.00019 |
| 17(22) | 32 | 0.00017 |
| 17(23) | 32 | 0.00016 |
| 17(24) | 32 | 0.00019 |
| 17(25) | 32 | 0.00020 |

Many of the altered forms of SEQ ID NO: 17 described in Table 4 exhibited inhibitory activity against chymase. The aptamers exhibiting $IC_{50}$ values of 0.001 μM or less, in particular, can be judged to have an excellent inhibitory effect. From the results of SEQ ID NO: 17(11)-SEQ ID NO: 17(14), it was shown that the terminal modification does not influence the activity.

As for the nucleotides contained in the common sequence, the 2'-O-methyl modification of the second G in GGGG in the above-mentioned common sequence as in SEQ ID NO: 17(1) and SEQ ID NO: 17(3) resulted in a decrease in the activity even though the activity was sufficient as that of an aptamer, and it was shown that changes in the modification embodiment of this part affects the activity. On the other hand, it was shown that the 2'-O-methyl modification of G other than the second G in GGGG in the above-mentioned common sequence as in SEQ ID NO: 17(2) does not influence the activity.

From the results of the aptamers shown by SEQ ID NO: 17(1)-SEQ ID NO: 17(25), modification of sequence other than the second G of GGGG in the above-mentioned common sequence improves stability. Thus, it was found that at least one nucleotide of the aptamer of the present invention may be modified as long as the activity is maintained. As the modification of nucleotide, for example, 2'-amino modification and the like can be mentioned in addition to 2'-O-methyl modification.

From the above, SEQ ID NO: 17 altered by chemical modification has a strong chymase-inhibitory activity and was suggested to be usable as a chymase inhibitor.

Example 4: Effect of Base Insertion on Loop Structure of Aptamer

A base was inserted into the loop structure of the aptamer shown by SEQ ID NO: 2, and an influence on the binding activity and inhibitory activity was examined. The sequences are shown in SEQ ID NO: 21-SEQ ID NO: 25.

All nucleic acids of SEQ ID NO: 21-25 were prepared by chemical synthesis. The nucleotide sequences of respective aptamers shown by the following SEQ ID NO: 21-25 are shown below. Unless otherwise specified, the respective sequences recited below are in the direction of from 5' to 3', modification at the 2'-position of ribose is shown in the parenthesis (for example, U(F) shows modification of the 2'-position of ribose of uracil with F), and F is a fluorine atom.

SEQ ID NO: 21 sequence obtained by inserting 17 nucleic acid bases into loop structure of sequence shown by SEQ ID NO: 2

GGCAGAUGAUCGGACAUAACAGGUUAGAUAGAGUUAAAAACCUGGGGUGU

CAA

SEQ ID NO: 22 sequence obtained by inserting 15 nucleic acid bases into loop structure of sequence shown by SEQ ID NO: 2

GGCAGAUGAUCGGACAUAACAGUUAGAUAGAGUUAAAAACUGGGGUGUCA

A

SEQ ID NO: 23 sequence obtained by inserting 13 nucleic acid bases into loop structure of sequence shown by SEQ ID NO: 2

GGCAGAUGAUCGGACAUAACAGUAGAUAGAGUUAAAACUGGGGUGUCAA

SEQ ID NO: 24 sequence obtained by inserting 11 nucleic acid bases into loop structure of sequence shown by SEQ ID NO: 2

GGCAGAUGAUCGGACAUAACAUAGAUAGAGUUAAAAUGGGGUGUCAA

SEQ ID NO: 25 sequence obtained by inserting 9 nucleic acid bases into loop structure of sequence shown by SEQ ID NO: 2

GGCAGAUGAUCGGACAUAACAAGAUAGAGUUAAAUGGGGUGUCAA

All nucleic acids of SEQ ID NO: 21-25 were prepared by chemical synthesis.

In the evaluation of SEQ ID NO: 21-25, a method similar to the evaluation method of inhibitory activity against chymase shown in Example 1 by using MCA as a substrate except that the amount chymase was changed from 0.05 μg to 0.005 μg was used for measurement. The measurement results are shown in Table 5. In the Table, the value of $IC_{50}$ is the value of one measurement.

TABLE 5

| SEQ ID NO: | number inserted into loop structure | IC50 [μM] |
| --- | --- | --- |
| 21 | 17 | 0.0057 |
| 22 | 15 | 0.0050 |
| 23 | 13 | 0.0078 |
| 24 | 11 | 0.0037 |
| 25 | 9 | 0.0058 |

The sequences of Table 5 showed an inhibitory activity against chymase. All showed an $IC_{50}$ value of not more than 0.01 μM and an inhibitory effect. It was found that the insertion of up to 17 bases into the loop structure of SEQ ID NO: 2 resulted in the maintenance of activity.

Example 5: Production of RNA Aptamer by Optimized SELEX

Optimized SELEX was performed to obtain aptamers that specifically bind to chymase and have higher activity. The optimized SELEX was the same as the SELEX described in Example 1 except for the DNA template and primers described below.

Figure 5:
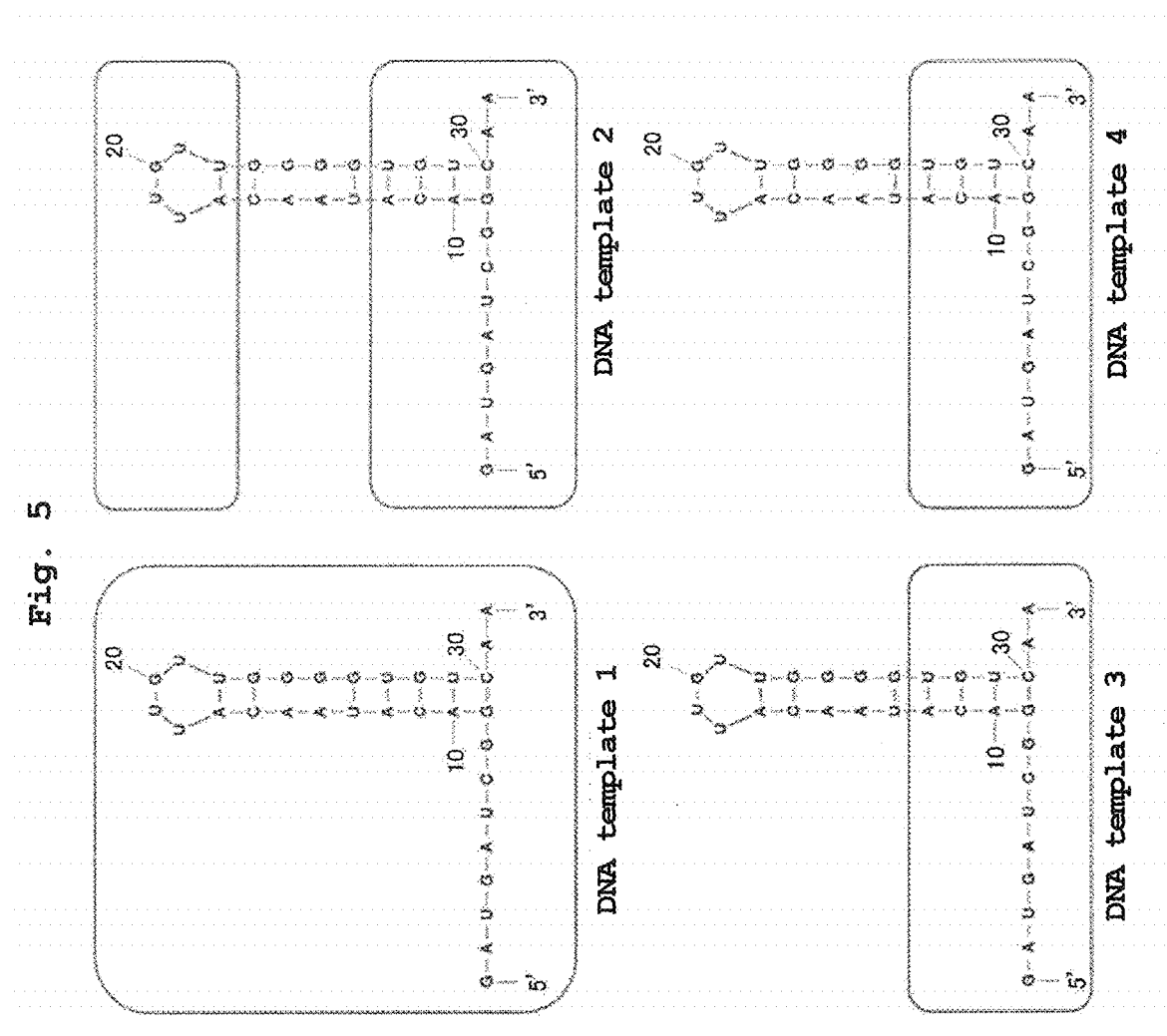
FIG. 5 shows random sequence parts of DNA templates in optimized SELEX.

The DNA templates used were 4 kinds of DNA templates prepared by chemical synthesis based on SEQ ID NO: 17 obtained in Example 2, by forming a random sequence as a part of the sequence. The primers used were SEQ ID NO: 35 and SEQ ID NO: 36 used in Example 1. FIG. 5 shows random sequence parts (surrounded by square) of the DNA templates.

DNA template:

(SEQ ID NO: 40)
5'-TCACACTAGCACGCATAGGCCTTGACACCCCAACAATGTTATGTCCG

ATCATCTGACCTCTCTCCTGCTCCC-3'

DNA template 1: template in which a part surrounded by square of SEQ ID NO: 17 is doped with 9% random sequence (A, G, C or T in any combination of nucleotides)

DNA template 2: template in which a part surrounded by square of SEQ ID NO: 17 is doped with 9% random sequence (A, G, C or T in any combination of nucleotides)

DNA template 3: template in which a part surrounded by square of SEQ ID NO: 17 is doped with 15% random sequence (A, G, C or T in any combination of nucleotides)
DNA template 4: template in which a part surrounded by square of SEQ ID NO: 17 is random sequence (A, G, C or T in any combination of nucleotides)

Figure 6:
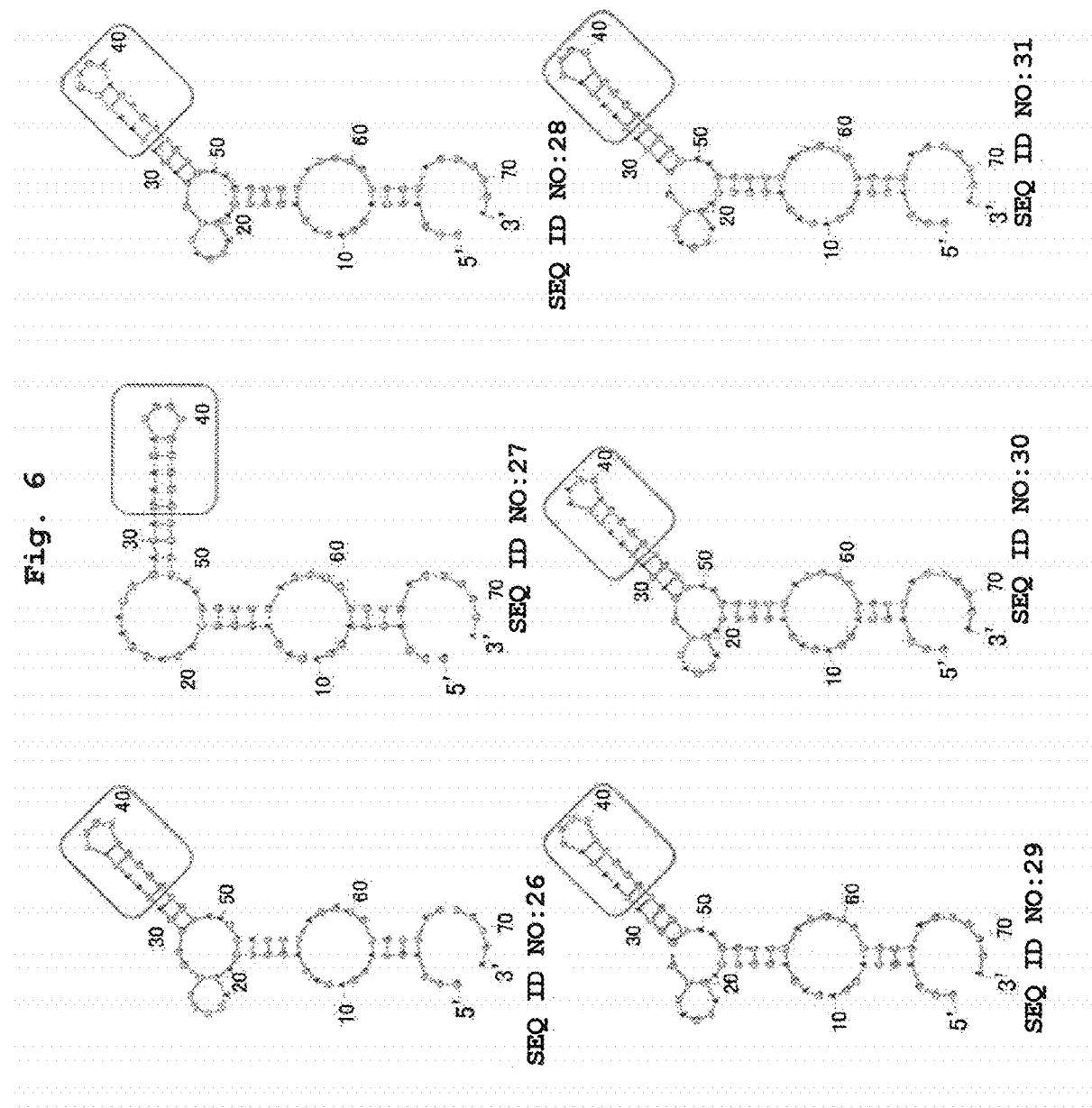
FIG. 6 shows the predicted secondary structures of the aptamers of the sequences shown by SEQ ID NO: 26-31.

After 6 rounds of SELEX using DNA template 1 and DNA template 2, the sequences of 48 clones were examined to find sequence convergence. Similarly, after 3 rounds of SELEX using DNA template 3 and DNA template 4, the sequences of 32 clones were examined to find sequence convergence. The sequences of some of the clones are shown by SEQ ID NO: 26-31. The predicted secondary structures of the aptamers of the sequences shown by SEQ ID NO: 26-31 are shown in FIG. 6. The stem-loop structure represented by the formula (1) is surrounded by a square (□).

Given below are the respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 26
GGGAGCAGGAGAGAGGUCAGAUUUUCGGGCAUAACAUUGUUGGGGUGUAA

CGACCUAUGCGUGCUAGUGUGA

SEQ ID NO: 27
GGGAGCAGGAGAGAGGUCAGAUGAACGGACAUAACAUUGUUGGGGUGUCA

AGGCCUAUGCGUGCUAGUGUGA

SEQ ID NO: 28
GGGAGCAGGAGAGAGGUCAGAUGAUCGGACAUAACUCUGGAGGGGUGUCA

AGGCCUAUGCGUGCUAGUGUGA

SEQ ID NO: 29
GGGAGCAGGAGAGAGGUCAGAUGAUCGGGCAUAACAUUGUUGGGGUGUCA

AGGCCUAUGCGUGCUAGUGUGA

SEQ ID NO: 30
GGGAGCAGGAGAGAGGUCAGAUGAUCGGACAUAACUAAUUAGGGGUGUCA

AGGCCUAUGCGUGCUAGUGUGA

SEQ ID NO: 31
GGGAGCAGGAGAGAGGUCAGAUGAUCGGACAUAACAUUGCUGGGGUGUCA

AGGCCUAUGCGUGCUAGUGUGA

All nucleic acids of SEQ ID NO: 26-31 were prepared by chemical synthesis. The aptamers shown by these sequences exhibited activity similar to that of the aptamers shown in Example 2.

Example 6: Shortening of Aptamer Obtained by Optimized SELEX

The aptamer shown by SEQ ID NO: 30 was shortened. The aptamer shown by SEQ ID NO: 30 contains the common sequence. The shortened sequences are shown in SEQ ID NO: 32-33. The predicted secondary structures of the aptamers shown by SEQ ID NO: 32-33 are shown in FIG. 7. In FIG. 7, the stem-loop structure represented by the formula (1) is surrounded by a square (□).

Respective nucleotide sequences shown in SEQ ID NOs: 32-33 are presented below. Unless particularly indicated, the sequences shown below are in the 5' to 3' direction, purine bases (A and G) are 2'-OH forms and pyrimidine bases (U and C) are 2'-fluoro modified forms.

SEQ ID NO: 32
sequence obtained by shortening sequence shown by SEQ ID NO: 30 to length of 32 nucleotides containing common sequence

GAUGAUCGGACAUAACUAAUUAGGGGUGUCAA

SEQ ID NO: 33
sequence obtained by shortening sequence shown by SEQ ID NO: 30 to length of 31 nucleotides containing common sequence

AUGAUCGGACAUAACUAAUUAGGGGUGUCAA

All nucleic acids of SEQ ID NO: 32-33 were prepared by chemical synthesis. The aptamers shown by these sequences exhibited activity similar to that of the aptamers shown in Example 2.

Example 7: Alteration of Aptamer Obtained by Optimized SELEX and Shortening

To enhance nuclease resistance of the aptamer shown by SEQ ID NO: 33, an altered aptamer with terminal modification, an altered aptamer wherein the 2'-position of ribose of purine base in the sequence is modified with O-methyl group or F, and an altered aptamer wherein phosphorothioate is introduced were prepared. The sequences are shown in SEQ ID NO: 33(1)-33(18).

The respective nucleotide sequences are shown below. Unless otherwise specified, the respective sequences recited below are in the direction of from 5' to 3', modification at the 2'-position of ribose is shown in the parenthesis, F is a fluorine atom, M is an O-methyl group, and PHE is 8-(Propyl)phenyl-rA(n-bz)-2'-tBDMS amidite. In respective sequence terminals, idT shows modification with inverted-dT, PEG shows modification with 40 kDa branched polyethylene glycol, and S shows modification with a thiol group.

SEQ ID NO: 33(1)
sequence obtained by introducing idT modification into 5'-terminal and 3'-terminal, introducing 2'-O-methyl modification into 15 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)AAU(F)U(M)AG(M)GG(M)G(M)TG(M)U(M)C(M)A (M)A(M)-idT

SEQ ID NO: 33(2)
sequence obtained by introducing idT modification into 5'-terminal and 3'-terminal, introducing 2'-O-methyl modification into 13 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

```
idT-
A(M)U(M)G(M)A(M)U(F)C(F)G(M)G(M)A(M)C(F)A(M)U(M)
AAC(M)U(F)AAU(F)U(M)AG(M)GG(M)G(M)TG(M)TC(M)A(M)
A(M)-idT
```

SEQ ID NO: 33(3)
sequence obtained by introducing idT modification into 5'-terminal and 3'-terminal, introducing 2'-O-methyl modification into 17 positions and 8-(propyl)phenyl-rA(n-bz)-2'-tBDMS amidite modification into one position in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

```
idT-
A(PHE)U(M)G(M)A(M)U(F)C(F)G(M)G(M)A(M)C(M)A(M)U
(M)AAC(M)U(F)A(M)A(M)U(F)U(M)A(M)G(M)GG(M)G(M)TG
(M)U(M)C(M)A(M)A(M)-idT
```

SEQ ID NO: 33(4)
sequence obtained by introducing idT modification into 5'-terminal and 3'-terminal, introducing 2'-O-methyl modification into 15 positions and 8-(propyl)phenyl-rA(n-bz)-2'-tBDMS amidite modification into one position in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

```
idT-
A(PHE)U(M)G(M)A(M)U(F)C(F)G(M)G(M)A(M)C(F)A(M)U(M)
AAC(M)1J(F)A(M)A(M)U(F)U(M)A(M)G(M)GG(M)G(M)TG(M)
TC(M)A(M)A(M)-idT
```

SEQ ID NO: 33(5)
sequence obtained by introducing idT modification into 5'-terminal and 3'-terminal, introducing 2'-O-methyl modification into 16 positions and 8-(propyl)phenyl-rA(n-bz)-2'-tBDMS amidite modification into one position in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

```
idT-
A(PHE)U(M)G(M)A(M)U(F)C(F)G(M)G(M)A(M)C(F)A(M)U(M)
AAC(M)U(F)A(M)A(M)U(F)U(M)A(M)G(M)GG(M)G(M)TG(M)
U(M)C(M)A(M)A(M)-idT
```

SEQ ID NO: 33(6)
sequence obtained by introducing idT modification into 5'-terminal and 3'-terminal, introducing 2'-O-methyl modification into 18 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

```
idT-
A(M)U(M)G(M)A(M)U(F)C(F)G(M)G(M)A(M)C(F)A(M)U(M)
AAC(M)U(F)A(M)A(M)U(M)U(M)A(M)G(M)GG(M)G(M)TG(M)
U(M)C(M)A(M)A(M)-idT
```

SEQ ID NO: 33(7)
sequence obtained by introducing idT modification into 5'-terminal and 3'-terminal, introducing 2'-O-methyl modification into 19 positions in the sequence other than the common sequence, introducing 2'-O-methyl modification into nucleotides other than the second A of the common sequence UAAC, and introducing 2'-O-methyl modification into G other than the second G in the common sequence GGGG, of the sequence shown by SEQ ID NO: 33

```
idT-
A(M)U(M)G(M)A(M)U(F)C(F)G(M)G(M)A(M)C(M)A(M)U(M)
A(M)AC(M)U(F)A(M)A(M)U(M)U(M)A(M)G(M)GG(M)G(M)
TG(M)U(M)C(M)A(M)A(M)-idT
```

SEQ ID NO: 33(8)
sequence obtained by introducing idT modification into 5'-terminal and 3'-terminal, introducing 2'-O-methyl modification into 19 positions in the sequence other than the common sequence, introducing 2'-O-methyl modification into nucleotides other than the first A of the common sequence UAAC, and introducing 2'-O-methyl modification into G other than the second G in the common sequence GGGG, of the sequence shown by SEQ ID NO: 33

```
idT-
A(M)U(M)G(M)A(M)U(F)C(F)G(M)G(M)A(M)C(M)A(M)U(M)
AA(M)C(M)U(F)A(M)A(M)U(M)U(M)A(M)G(M)GG(M)G(M)
TG(M)U(M)C(M)A(M)A(M)-idT
```

SEQ ID NO: 33(9)
sequence obtained by introducing idT modification into 5'-terminal and 3'-terminal, introducing 2'-O-methyl modification into 19 positions in the sequence other than the common sequence, introducing 2'-O-methyl modification into U and C in the common sequence UAAC, and introducing 2'-O-methyl modification into common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)U(M)U(M)A(M)G(M)G(M)G(M)G(M)

tG(M)U(M)C(M)A(M)A(M)-idT

SEQ ID NO: 33(10)

sequence obtained by introducing idT modification into 5'-terminal and 3'-terminal, introducing 2'-O-methyl modification into 19 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)TA(M)A(M)U(M)U(M)A(M)G(M)GG(M)G(M)TG(M)U(M)

C(M)A(M)A(M)-idT

SEQ ID NO: 33(11)

sequence obtained by introducing idT modification into 5'-terminal and 3'-terminal, introducing 2'-O-methyl modification into 18 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)TU(M)A(M)G(M)GG(M)G(M)TG(M)U(M)

C(M)A(M)A(M)-idT

SEQ ID NO: 33(12)

sequence obtained by introducing idT modification into 5'-terminal and 3'-terminal, introducing 2'-O-methyl modification into 18 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)U(M)TA(M)G(M)GG(M)G(M)TG(M)U(M)

C(M)A(M)A(M)-idT

SEQ ID NO: 33(13)

sequence obtained by introducing idT modification into 5'-terminal and 3'-terminal, introducing 2'-O-methyl modification into 20 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)T(M)A(M)A(M)U(M)U(M)A(M)G(M)GG(M)G(M)TG(M)

U(M)C(M)A(M)A(M)-idT

SEQ ID NO: 33(14)

sequence obtained by introducing idT modification into 5'-terminal and 3'-terminal, introducing 2'-O-methyl modification into 19 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)T(M)U(M)A(M)G(M)GG(M)G(M)TG(M)

U(M)C(M)A(M)A(M)-idT

SEQ ID NO: 33(15)

sequence obtained by introducing idT modification into 5'-terminal and 3'-terminal, introducing 2'-O-methyl modification into 19 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)U(M)T(M)A(M)G(M)GG(M)G(M)TG(M)

U(M)C(M)A(M)A(M)-idT

SEQ ID NO: 33(16)

sequence obtained by introducing idT modification into 5'-terminal and 3'-terminal, introducing 2'-O-methyl modification into 20 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(M)U(M)G(M)A(M)U(F)C(F)G(M)G(M)A(M)C(M)A(M)U(M)

AAC(M)U(F)A(M)A(M)U(M)U(M)A(M)G(M)GG(M)G(M)T(M)

G(M)U(M)C(M)A(M)A(M)-idT

SEQ ID NO: 33(17)

sequence obtained by introducing idT modification into 5'-terminal and 3'-terminal, introducing 2'-O-methyl modification into 18 positions and 8-(propyl)phenyl-rA(n-bz)-2'-tBDMS amidite modification into one position in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33 idT-

A(PHE)U(M)G(M)A(M)U(F)C(F)G(M)G(M)A(M)C(M)A(M)U(M)

AAC(M)U(F)A(M)A(M)U(M)U(M)A(M)G(M)GG(M)G(M)TG(M)

U(M)C(M)A(M)A(M)-idT

SEQ ID NO: 33(18)

sequence obtained by introducing 40 kDa branched polyethylene glycol modification into 5'-terminal, introducing idT modification into 3'-terminal, introducing 2'-O-methyl modification into 18 positions in the sequence other than the common sequence, introducing 2'-O-methyl modification into U and C in the common sequence UAAC, and introducing 2'-O-methyl modification into G other than the second G in the common sequence GGGG, of the sequence shown by SEQ ID NO: 33

PEG-

A(M)U(M)G(M)A(M)U(F)C(F)G(M)G(M)A(M)C(M)A(M)U(M)

AAC(M)U(F)A(M)A(M)U(M)TA(M)G(M)GG(M)G(M)TG(M)U(M)

C(M)A(M)A(M)-idT

All nucleic acids of SEQ ID NO: 33(1)-33(18) were prepared by chemical synthesis. The aptamers shown by these sequences were measured by a method similar to the inhibitory activity evaluation method for chymase inhibitory activity shown in Example 1 by using angiotensin I as a substrate. The results are shown in Table 6. In the Table, the $IC_{50}$ value is a mean of 2 or 3 measurements.

TABLE 6

| SEQ ID NO: | length | IC50 [μM] |
| --- | --- | --- |
| 2 | 72 | 0.010000 |
| 17 | 32 | 0.001400 |
| 33 | 32 | 0.000210 |
| 33(1) | 31 | 0.000074 |
| 33(2) | 31 | 0.000078 |
| 33(3) | 31 | 0.000071 |
| 33(4) | 31 | 0.000072 |
| 33(5) | 31 | 0.000076 |
| 33(6) | 31 | 0.000053 |
| 33(7) | 31 | 0.000071 |
| 33(8) | 31 | 0.000061 |
| 33(9) | 31 | 0.001355 |
| 33(10) | 31 | 0.000071 |

TABLE 6-continued

| SEQ ID NO: | length | IC50 [μM] |
| --- | --- | --- |
| 33(11) | 31 | 0.000051 |
| 33(12) | 31 | 0.000048 |
| 33(13) | 31 | 0.000069 |
| 33(14) | 31 | 0.000075 |
| 33(15) | 31 | 0.000072 |
| 33(16) | 31 | 0.000063 |
| 33(17) | 31 | 0.000038 |
| 33(18) | 31 | 0.000109 |

As shown in Table 6, many of the altered forms exhibited inhibitory activity against chymase. The aptamers exhibiting $IC_{50}$ values of 0.0001 μM or less, in particular, can be judged to have a very superior inhibitory effect. From the above, it was found that at least one nucleotide of the aptamer may be modified to increase the stability of the aptamer of the sequence shown by SEQ ID NO: 33 with various modifications applied thereon as long as its activity is ensured. As the modification of nucleotide, for example, 2'-amino modification and the like can be mentioned in addition to 2'-O-methyl modification.

As for the nucleotides contained in the common sequence, the 2'-O-methyl modification of the second G in the common sequence GGGG as in SEQ ID NO: 33(9) resulted in a decrease in the activity as compared to other modified aptamer having sequence SEQ ID NO: 33, even though the activity was sufficient as that of an aptamer. On the other hand, modification as in SEQ ID NO: 33(12) did not influence the activity.

From the results of SEQ ID NO: 33(18), a certain level of the activity of PEG-bound aptamer was maintained as compared to the aptamer not bound with PEG (SEQ ID NO: 33(12)). Since binding with PEG markedly improves in vivo pharmacokinetics, an in vivo effect is expected from the results.

From the above results, any nucleic acid contained in Table 6 other than nucleic acid in which the 2nd G of GGGG in the common sequence is modified with 2'-O-methyl is expected as a drug for the prophylaxis and/or treatment of various diseases involving angiotensin, since it shows an extremely strong chymase inhibitory activity even when angiotensin I, a native substrate, is used.

INDUSTRIAL APPLICABILITY

The aptamer of the present invention can be useful as a pharmaceutical for preventing and/or treating various diseases involving activation of TGF-β such as fibrosis and the like, or a diagnostic reagent or a labeling agent.

This application is based on a patent application No. 2017-230503 filed in Japan (filing date: Nov. 30, 2017), the contents of which are incorporated in full herein.

The invention claimed is:

1. An aptamer that binds to chymase, and comprises a potential secondary structure represented by the formula (1), wherein uracil is optionally thymine:

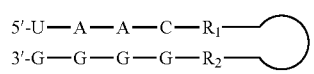

(1)

wherein

(1')

in the formula (1) is a stem-loop partial structure, and $R_1$ and $R_2$ are each any one base, wherein a base length of the aptamer is not less than 28, the stem-loop partial structure of (1') has a base length of 3-21, and at least two bases at the 5' end of the UAAC sequence and at least two bases at the 3' end of the GGGG sequence form base pairs, and wherein the aptamer comprises a nucleotide sequence selected from any of SEQ ID NOs: 1-11 and 14-33, wherein uracil is optionally thymine.

2. The aptamer according to claim 1, wherein a hydroxyl group at the 2'-position of ribose of each pyrimidine nucleotide contained in the aptamer is the same or different and unsubstituted or substituted by an atom or a group selected from the group consisting of a hydrogen atom, a fluorine atom and a methoxy group.

3. The aptamer according to claim 1, wherein a hydroxyl group at the 2'-position of ribose of each purine nucleotide contained in the aptamer is the same or different and unsubstituted or substituted by an atom or a group selected from the group consisting of a hydrogen atom, a fluorine atom and a methoxy group.

4. A complex comprising the aptamer and the functional substance according to claim 1.

5. A medicament comprising the aptamer according to claim 1.

6. The medicament according to claim 5 that is a therapeutic drug for a disease involving organ or tissue fibrosis, or a circulatory disease.

7. The medicament according to claim 5 that is a therapeutic drug for fibrosis.

8. A method for detecting chymase, comprising using the aptamer according to claim 1.

* * * * *

SEQUENCE LISTING

```
<160> NUMBER OF SEQ ID NOS: 41

<210> SEQ ID NO 1
<211> LENGTH: 72
<212> TYPE: RNA
<213> ORGANISM: Artificial Sequence
<220> FEATURE:
<223> OTHER INFORMATION: Synthetic Sequence - aptamer against chymase
```

<400> SEQUENCE: 1
gggagcagga gagaggucag augagcaugc uuuuugguaa ccgauaaugg gggccuaugc    60
gugcuagugu ga                                                      72

<210> SEQ ID NO 2
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 2
gggagcagga gagaggucag augaucggac auaacauugu uggggugauca aggccuaugc    60 gugcuagugu ga                                                      72

<210> SEQ ID NO 3
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 3
gggagcagga gagaggucag augauaacca guugggggu caauuacaug ggaccuaugc    60
gugcuagugu ga                                                      72

<210> SEQ ID NO 4
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 4
gggagcagga gagaggucag auguaacucu auugaggggc aucagcacag uagccuaugc    60
gugcuagugu ga                                                      72

<210> SEQ ID NO 5
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 5
gggagcagga gagaggucag augaugaccg auuauaggua accacuuagg gggccuaugc    60
gugcuagugu ga                                                      72

<210> SEQ ID NO 6
<211> LENGTH: 72
<212> TYPE: RNA
<213> ORGANISM: Artificial Sequence
<220> FEATURE:
<223> OTHER INFORMATION: Synthetic Sequence

<400> SEQUENCE: 6
gggagcagga gagaggucag augucaugac uuauagguaa ccgauaaugg gggccuaugc    60
gugcuagugu ga                                                      72

<210> SEQ ID NO 7

```
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 7
gggagcagga gagaggucag auguuuggua guaacuggaa uaggggcuac aggccuaugc    60
gugcuagugu ga                                                       72

<210> SEQ ID NO 8
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 8
gggagcagga gagaggucag augauugacg acuauaggua accuuuacgg gggccuaugc    60
gugcuagugu ga                                                       72

<210> SEQ ID NO 9
<211> LENGTH: 77
<212> TYPE: RNA
<213> ORGANISM: Artificial Sequence
<220> FEATURE:
<223> OTHER INFORMATION: Synthetic Sequence - aptamer against chymase

<400> SEQUENCE: 9
gggaacgaag cgacagacgu uccagcgucu aauacgugaa uaaccugauc guaggggguu    60
caaguacuga ggacaga                                                  77

<210> SEQ ID NO 10
<211> LENGTH: 76
<212> TYPE: RNA
<213> ORGANISM: Artificial Sequence
<220> FEATURE:
<223> OTHER INFORMATION: Synthetic Sequence - aptamer against chymase

<400> SEQUENCE: 10
gggaacgaag cgacagaccg aaucagaagu ucaacaugga cauaacaucg auggguguc    60 aaguacugac gacaga                                                   76

<210> SEQ ID NO 11
<211> LENGTH: 43
<212> TYPE: RNA
<213> ORGANISM: Artificial Sequence
<220> FEATURE:
<223> OTHER INFORMATION: Synthetic Sequence - aptamer against chymase

<400> SEQUENCE: 11
gggucagaug aucggacaua acauuguugg ggugucaagg ccc                     43

<210> SEQ ID NO 12
<211> LENGTH: 22
<212> TYPE: RNA
<213> ORGANISM: Artificial Sequence
<220> FEATURE:
<223> OTHER INFORMATION: Synthetic Sequence - nucleotide sequence not
      binding to chymase

<400> SEQUENCE: 12
gacauaacau uguuggggug uc                                            22
```

```
<210> SEQ ID NO 13
<211> LENGTH: 27
<212> TYPE: RNA
<213> ORGANISM: Artificial Sequence
<220> FEATURE:
<223> OTHER INFORMATION: Synthetic Sequence - nucleotide sequence not
      binding to chymase

<400> SEQUENCE: 13
ggacauaaca uguuggggu gucaagg                                           27

<210> SEQ ID NO 14
<211> LENGTH: 39
<212> TYPE: RNA
<213> ORGANISM: Artificial Sequence
<220> FEATURE:
<223> OTHER INFORMATION: Synthetic Sequence - aptamer against chymase

<400> SEQUENCE: 14
ggcagaugau cggacauaac auuguugggg ugucaagcc                             39

<210> SEQ ID NO 15
<211> LENGTH: 35
<212> TYPE: RNA
<213> ORGANISM: Artificial Sequence
<220> FEATURE:
<223> OTHER INFORMATION: Synthetic Sequence - aptamer against chymase

<400> SEQUENCE: 15
gaugaucgga cauaacauug uuggggguguc aagcc                                35

<210> SEQ ID NO 16
<211> LENGTH: 36
<212> TYPE: RNA
<213> ORGANISM: Artificial Sequence
<220> FEATURE:
<223> OTHER INFORMATION: Synthetic Sequence - aptamer against chymase

<400> SEQUENCE: 16
ggcagaugau cggacauaac auuguugggg ugucaa                                36

<210> SEQ ID NO 17
<211> LENGTH: 32
<212> TYPE: RNA
<213> ORGANISM: Artificial Sequence
<220> FEATURE:
<223> OTHER INFORMATION: Synthetic Sequence - aptamer against chymase

<400> SEQUENCE: 17
gaugaucgga cauaacauug uugggguguc aa                                    32

<210> SEQ ID NO 18
<211> LENGTH: 30
<212> TYPE: RNA
<213> ORGANISM: Artificial Sequence
<220> FEATURE:
<223> OTHER INFORMATION: Synthetic Sequence - aptamer against chymase

<400> SEQUENCE: 18
ugaucggaca uaacauuguu gggguguca a                                      30

<210> SEQ ID NO 19
<211> LENGTH: 28
<212> TYPE: RNA
<213> ORGANISM: Artificial Sequence
<220> FEATURE:
```

<223> OTHER INFORMATION: Synthetic Sequence - aptamer against chymase

<400> SEQUENCE: 19
aucggacaua acauuguugg ggugucaa                                        28

<210> SEQ ID NO 20
<211> LENGTH: 31
<212> TYPE: RNA
<213> ORGANISM: Artificial Sequence
<220> FEATURE:
<223> OTHER INFORMATION: Synthetic Sequence - aptamer against chymase

<400> SEQUENCE: 20
gaugaucgga cauaacauug uuggggguguc a                                    31

<210> SEQ ID NO 21
<211> LENGTH: 53
<212> TYPE: RNA
<213> ORGANISM: Artificial Sequence
<220> FEATURE:
<223> OTHER INFORMATION: Synthetic Sequence - aptamer against chymase

<400> SEQUENCE: 21
ggcagaugau cggacauaac agguuagaua gaguuaaaaa ccugggguguu caa            53

<210> SEQ ID NO 22
<211> LENGTH: 51
<212> TYPE: RNA
<213> ORGANISM: Artificial Sequence
<220> FEATURE:
<223> OTHER INFORMATION: Synthetic Sequence - aptamer against chymase

<400> SEQUENCE: 22
ggcagaugau cggacauaac aguuagauag aguuaaaaac ugggguguca a               51

<210> SEQ ID NO 23
<211> LENGTH: 49
<212> TYPE: RNA
<213> ORGANISM: Artificial Sequence
<220> FEATURE:
<223> OTHER INFORMATION: Synthetic Sequence - aptamer against chymase

<400> SEQUENCE: 23
ggcagaugau cggacauaac aguagauaga guuaaaacug ggugucaa                   49

<210> SEQ ID NO 24
<211> LENGTH: 47
<212> TYPE: RNA
<213> ORGANISM: Artificial Sequence
<220> FEATURE:
<223> OTHER INFORMATION: Synthetic Sequence - aptamer against chymase

<400> SEQUENCE: 24
ggcagaugau cggacauaac auagauagag uuaaaauggg gugucaa                    47

<210> SEQ ID NO 25
<211> LENGTH: 45
<212> TYPE: RNA
<213> ORGANISM: Artificial Sequence
<220> FEATURE:
<223> OTHER INFORMATION: Synthetic Sequence - aptamer against chymase

<400> SEQUENCE: 25
ggcagaugau cggacauaac aagauagagu uaaauggggu gucaa                      45

```
<210> SEQ ID NO 26
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 26
gggagcagga gagaggucag auuuucgggc auaacauugu ugggguguaa cgaccuaugc    60
gugcuagugu ga                                                       72

<210> SEQ ID NO 27
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 27
gggagcagga gagaggucag augaacggac auaacauugu ugggguguca aggccuaugc    60
gugcuagugu ga                                                       72

<210> SEQ ID NO 28
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 28
gggagcagga gagaggucag augaucggac auaacucugg aggggguguca aggccuaugc   60 gugcuagugu ga                                                       72

<210> SEQ ID NO 29
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 29
gggagcagga gagaggucag augaucgggc auaacauugu ugggguguca aggccuaugc    60
gugcuagugu ga                                                       72

<210> SEQ ID NO 30
<211> LENGTH: 72
<212> TYPE: RNA
<213> ORGANISM: Artificial Sequence
<220> FEATURE:
<223> OTHER INFORMATION: Synthetic Sequence - aptamer against chymase

<400> SEQUENCE: 30
gggagcagga gagaggucag augaucggac auaacuaauu aggggguguca aggccuaugc   60 gugcuagugu ga                                                       72

<210> SEQ ID NO 31
<211> LENGTH: 72
<212> TYPE: RNA
<213> ORGANISM: Artificial Sequence
<220> FEATURE:
<223> OTHER INFORMATION: Synthetic Sequence - aptamer against chymase
```

<400> SEQUENCE: 31
gggagcagga gagaggucag augaucggac auaacauugc uggggguguca aggccuaugc    60 gugcuagugu ga    72

<210> SEQ ID NO 32
<211> LENGTH: 32
<212> TYPE: RNA
<213> ORGANISM: Artificial Sequence
<220> FEATURE:
<223> OTHER INFORMATION: Synthetic Sequence - aptamer against chymase

<400> SEQUENCE: 32
gaugaucgga cauaacuaau uaggggguguc aa    32

<210> SEQ ID NO 33
<211> LENGTH: 31
<212> TYPE: RNA
<213> ORGANISM: Artificial Sequence
<220> FEATURE:
<223> OTHER INFORMATION: Synthetic Sequence - aptamer against chymase

<400> SEQUENCE: 33
augaucggac auaacuaauu agggguguca a    31

<210> SEQ ID NO 34
<211> LENGTH: 72
<212> TYPE: DNA
<213> ORGANISM: Artificial Sequence
<220> FEATURE:
<223> OTHER INFORMATION: Synthetic Sequence - DNA template
<220> FEATURE:
<221> NAME/KEY: misc_feature
<222> LOCATION: (20)..(49)
<223> OTHER INFORMATION: n is a, c, g, or t

<400> SEQUENCE: 34
tcacactagc acgcataggn nnnnnnnnn nnnnnnnnnn nnnnnnnnnc atctgacctc    60
tctcctgctc cc    72

<210> SEQ ID NO 35
<211> LENGTH: 40
<212> TYPE: DNA
<213> ORGANISM: Artificial Sequence
<220> FEATURE:
<223> OTHER INFORMATION: Synthetic Sequence - primer Fwd

<400> SEQUENCE: 35
taatacgact cactataggg agcaggagag aggtcagatg    40

<210> SEQ ID NO 36
<211> LENGTH: 19
<212> TYPE: DNA
<213> ORGANISM: Artificial Sequence
<220> FEATURE:
<223> OTHER INFORMATION: Synthetic Sequence - primer Rev

<400> SEQUENCE: 36
tcacactagc acgcatagg    19

<210> SEQ ID NO 37
<211> LENGTH: 76
<212> TYPE: DNA
<213> ORGANISM: Artificial Sequence
<220> FEATURE:

```
<223> OTHER INFORMATION: Synthetic Sequence - DNA template
<220> FEATURE:
<221> NAME/KEY: misc_feature
<222> LOCATION: (19)..(58)
<223> OTHER INFORMATION: n is a, c, g, or t

<400> SEQUENCE: 37
tctgtcctca gtacttgann nnnnnnnnnn nnnnnnnnnn nnnnnnnnnn nnnnnnnngt    60
ctgtcgcttc gttccc                                                    76

<210> SEQ ID NO 38
<211> LENGTH: 35
<212> TYPE: DNA
<213> ORGANISM: Artificial Sequence
<220> FEATURE:
<223> OTHER INFORMATION: Synthetic Sequence - primer Fwd

<400> SEQUENCE: 38
taatacgact cactataggg aacgaagcga cagac                                35

<210> SEQ ID NO 39
<211> LENGTH: 18
<212> TYPE: DNA
<213> ORGANISM: Artificial Sequence
<220> FEATURE:
<223> OTHER INFORMATION: Synthetic Sequence - primer Rev

<400> SEQUENCE: 39
tctgtcctca gtacttga                                                   18

<210> SEQ ID NO 40
<211> LENGTH: 72
<212> TYPE: DNA
<213> ORGANISM: Artificial Sequence
<220> FEATURE:
<223> OTHER INFORMATION: Synthetic Sequence - DNA template

<400> SEQUENCE: 40
tcacactagc acgcataggc cttgacaccc caacaatgtt atgtccgatc atctgacctc    60
tctcctgctc cc                                                         72

<210> SEQ ID NO 41
<211> LENGTH: 4
<212> TYPE: PRT
<213> ORGANISM: Artificial Sequence
<220> FEATURE:
<223> OTHER INFORMATION: Synthetic Sequence - Substrate for Chymotrypsin

<400> SEQUENCE: 41

Ala Ala Pro Phe
1
```